US010525167B2

(12) United States Patent
Apicella et al.

(10) Patent No.: US 10,525,167 B2
(45) Date of Patent: Jan. 7, 2020

(54) LOW VISCOSITY EMD

(71) Applicant: STRAUMANN HOLDING AG, Basel (CH)

(72) Inventors: Alessandra Apicella, Lausanne (CH); Peggy Heunemann, Obersiggenthal (CH)

(73) Assignee: STRAUMANN HOLDING AG, Basel (CH)

( * ) Notice: Subject to any disclaimer, the term of this patent is extended or adjusted under 35 U.S.C. 154(b) by 28 days.

(21) Appl. No.: 15/323,283

(22) PCT Filed: Jul. 9, 2015

(86) PCT No.: PCT/EP2015/065694
§ 371 (c)(1),
(2) Date: Dec. 30, 2016

(87) PCT Pub. No.: WO2016/005495
PCT Pub. Date: Jan. 14, 2016

(65) Prior Publication Data
US 2018/0169303 A1    Jun. 21, 2018

(30) Foreign Application Priority Data
Jul. 9, 2014    (SE) .................................. 1450883

(51) Int. Cl.
*A61L 27/54* (2006.01)
*A61K 38/39* (2006.01)
*A61K 47/12* (2006.01)
*A61L 27/56* (2006.01)

(52) U.S. Cl.
CPC .............. *A61L 27/54* (2013.01); *A61K 38/39* (2013.01); *A61K 47/12* (2013.01); *A61L 27/56* (2013.01);
(Continued)

(58) Field of Classification Search
CPC ...... A61K 38/39; A61K 47/12; A61L 2430/12; A61L 27/56; A61L 2400/12; A61L 27/54
See application file for complete search history.

(56) References Cited

U.S. PATENT DOCUMENTS

2010/0233783 A1*   9/2010   Svensson ................. C07K 1/14
                                                        435/201

FOREIGN PATENT DOCUMENTS

WO    WO01/97834 A1    12/2001
WO    WO01/97835 A1    12/2001
(Continued)

OTHER PUBLICATIONS

Buchko, G. W., et al., "A Solution NMR Investigation into the Early Events of Amelogenin Nanosphere Self-Assembly Initiated with Sodium Chloride or Calcium Chloride," Biochem. 2008;47:13215-13222.
(Continued)

*Primary Examiner* — Jianfeng Song
(74) *Attorney, Agent, or Firm* — Cermak Nakajima & McGowan LLP; Malcolm K. McGowan

(57) ABSTRACT

The present invention discloses a low viscosity composition comprising enamel matrix derivative (EMD) proteins in a suitable pharmaceutical carrier, said composition having a pH between pH 3.8-4.2, and a viscosity of less than 50 mPa s at 22° C., which, when applied to a porous bone graft material, improves and/or enhances bioactivity and osteoconduction of said bone graft material. The present invention consequently discloses a bone graft material which has been bioactivated using a low viscosity composition comprising enamel matrix derivative (EMD) proteins and which displays enhanced biocompatibility and improved bone regeneration after implantation.

5 Claims, 14 Drawing Sheets

Figure 1:
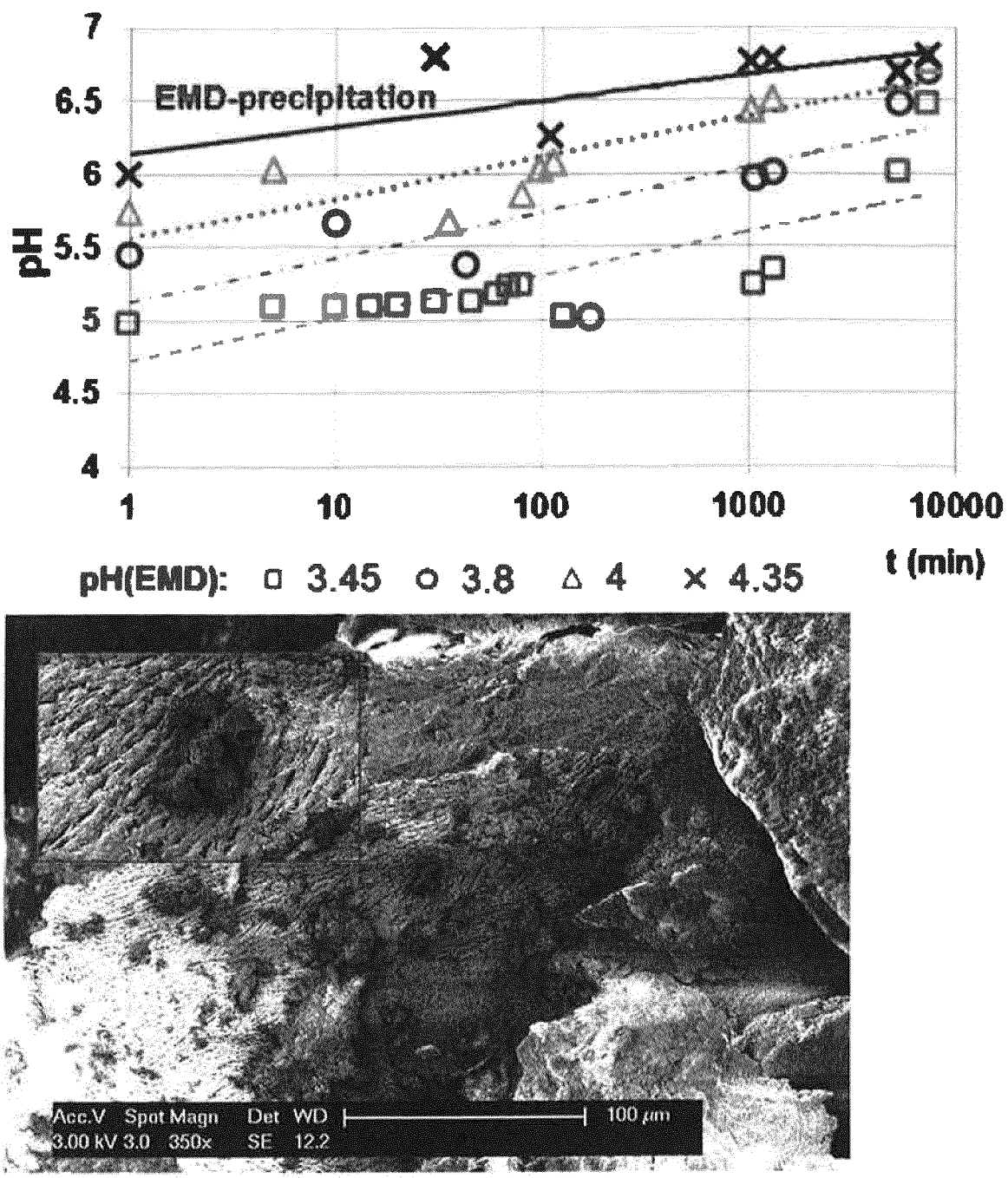

(52) U.S. Cl.
CPC ....... *A61L 2400/12* (2013.01); *A61L 2430/12* (2013.01)

(56) References Cited

FOREIGN PATENT DOCUMENTS

| WO | WO03/024479 A1 | 3/2003 |
|---|---|---|
| WO | WO2012/049324 A2 | 4/2012 |
| WO | WO2015/106970 A1 | 7/2015 |

OTHER PUBLICATIONS

Camargo, P. M., et al., "The effectiveness of enamel matrix proteins used in combination with bovine porous bone mineral in the treatment of intrabony defects in humans," J. Clin. Periodontol. 2001;28:1016-1022.

Velasquez-Plata, D., et al., "Clinical Comparison of an Enamel Matrix Derivative Used Alone or in Combination With a Bovine-Derived Xenograft for the Treatment of Periodontal Osseous Defects in Humans," J. Periodontol. 2002;73:433-440.

Heijl, L., "Periodontal regenerative potential using enamel matrix proteins (EMDOGAIN)," Tandläkartidningen årg 1998;90(14):10 pp.

Gestrelius, S., et al., "Formulation of enamel matrix derivative for surface coating Kinetics and cell colonization," J. Clin. Periodontol. 1997;24:678-684.

Cochran, D. L., Straumann—Prof. David J. Cochran at Europerio 8, Straumann Osteogain, Jun. 18, 2015, www.straumann.com/europerio6, XP054976059, 1 pg.

Gestrelius, S., et al., "Emdogain—periodontal regeneration based on biomimicry," Clin. Oral Invest. 2000;4:120-125.

Zhang, Y., et al., "Bone grafting material in combination with Osteogain for bone repair: a rat histomorphometric study," Clin. Oral Invest. 2015, XP055211946, 7 pp.

* cited by examiner

LOW VISCOSITY EMD

CROSS-REFERENCE TO RELATED APPLICATIONS

This application is a National Stage Entry of PCT/EP2015/065694, filed Jul. 9, 2015, which claims priority from Swedish patent application 1450833-2, filed Jul. 9, 2014. The contents of these priority applications are incorporated herein by reference in their entirety.

FIELD OF THE INVENTION

The present invention relates to the field of bone graft materials for implantation into patients in need thereof and their bioactivation. The present invention further relates to a low viscosity composition comprising active enamel substances, which is herein used for bioactivating bone graft materials, and to a kit comprising said bone graft material in combination with said low viscosity composition comprising active enamel substances, as well as to the bioactivated bone graft material as such.

BACKGROUND OF THE INVENTION

Periodontal tissue diseases are defined as an inflammatory condition of the gum and the bone support surrounding the teeth, often leading to complications, such as to bone degradation, which in turn can impend the correct placement and fixation of dental implants after tooth loss.

Bone grafting is a surgical procedure that replaces missing bone after bone degradations and/or in order to repair bone fractures that are extremely complex, pose a significant health risk to the patient, and/or fail to heal properly. Bone grafting is currently employed to remedy bone degradation coursed by periodontal tissue diseases with varying success rates.

Bone substitutes are in general increasingly used in surgery as over two millions bone grafting procedures are performed worldwide per year. Autografts are still widely preferred for bone substitution, though the morbidity and the inherent limited availability are the main limitations. Allografts, i.e. banked bone, are osteoconductive and weakly osteoinductive, though there are still concerns about the residual infective risks, costs and donor availability issues. As an alternative, xenograft substitutes are cheaper, but their use provides contrasting results, so far. Often, bovine bone is used to replace missing bone structure; the major advantage is that larger quantities of bone can be easily acquired compared to bone of human origin. Ceramic-based synthetic bone substitutes are alternatively based on hydroxyapatite (HA) and tricalcium phosphates, and are widely used in the clinical practice. Indeed, despite being completely resorbable and weaker than cortical bone, they have exhaustively proven to be effective. Biomimetic HAs are the evolution of traditional HA and contain ions (carbonates, Si, Sr, Fl, Mg) that mimic natural HA (biomimetic HA). Injectable cements represent another evolution, enabling mininvasive techniques. Bone morphogenetic proteins (namely BMP2 and 7) are the only bone inducing growth factors approved for human use in spine surgery and for the treatment of tibial nonunion.

Most bone grafts are expected to be reabsorbed and replaced as the natural bone heals over a few months' time.

The principles involved in successful bone grafting include osteoconduction (guiding the reparative growth of the natural bone), osteoinduction (encouraging undifferentiated cells to become active osteoblasts), and osteogenesis (living bone cells in the graft material contribute to bone remodeling).

Bone graft materials are autografts, allografts, xenografts or synthetic grafts.

Autografts

Autologous (or autogenous) bone grafting involves utilizing bone obtained from the same individual receiving the graft. Bone can be harvested from non-essential bones, such as the iliac crest or the fibula, the chin, the ribs, the mandible and even parts of the skull. Autogenous bone possesses all the properties essential for bone formation: it is osteoconductive and osteoinductive, and it houses growth factors and osteogenic cells with no associated immune or infective-related risks. Autologous bone fractions are slowly replaced by newly formed host bone. The disadvantages of autografts are that a surgical donor site is required, leading to possible post-operative pain and complications. Also, they carry a likelihood of blood loss or hematomas, infection, fracture, neurovascular injury, as well as cosmetic deformity, at the explantation site, and longer operative time.

Also, autogenous bone availability in a patient represents a significant limit, especially in pediatric patients and in the elderly.

Allografts

Allograft biobanked bone represents a suitable alternative to autogenous bone, being derived from humans as well. Allograft bone can be collected from either living donors (patients total hip replacement surgery) or nonliving donors and must be processed within a bone tissue bank. Donor bone is osteoconductive, weakly osteoinductive (growth factors may still be present, depending on the processing). Also, allografts often require sterilization (gamma-irradiation), with detrimental effects on mechanical properties of bone, and deactivation of proteins normally found in healthy bone.

The limits of such transplants are costs, laborious procedure (tissue processing, harvesting), mechanical resistance (in freeze dried and irradiated), limited osteoinduction and risk of infection.

Xenografts

Xenograft bone substitutes have their origin from a species other than human, such as bovine bone (or porcine bone) which can be freeze dried or demineralized and deproteinized. Xenografts are usually only distributed as a calcified matrix. Coral based xenografts are mainly calcium carbonate (and an important proportion of fluorides, useful in the context of grafting to promote bone development) while natural human bone is made of hydroxyapatite along with calcium phosphate and carbonate. The coral material is thus either transformed industrially into hydroxyapatite through a hydrothermal process, yielding to a non-resorbable xenograft, or simply the process is omitted and the coralline material remains in its calcium carbonate state for better resorption of the graft by the natural bone. The coral xenograft is then saturated with growth enhancing gels and solutions. Xenografts have given good results in dentistry, but scarce validation is available in orthopedics.

Clinically available coral-based products are Interpore and Pro-osteon (Interpore International, Inc., Irvine, Calif.) as well as bovine derived products such as Bio-Oss (Geistlich Biomaterials, Geistlich, Switzerland), Osteograf-N (CeraMed Co., Denver, Colo.), and Endobon (Merck Co., Darmstadt, Germany).

BioOss® is a natural product with bovine origin. It is deproteinized and sintered. The material's total porosity is between 70-75% with a particle size of 250-1000 µm.

The advantages are the easy availability, the osteoconductivity, the good mechanical properties and low costs.

Synthetic Grafts

Hydroxyapatite and Tricalcium Phosphate

Generally, synthetic bone substitutes are calcium based substitutes, in particular, a mix of HA (Hydroxyapatite) and TCP (Tricalcium phosphate), HA is a relatively inert substance that is retained "in vivo" for prolonged periods of time, whereas the more porous TCP typically undergoes biodegradation within 6 weeks of its introduction into the area of bone formation. HA achieves very high mechanical strength, while TCP has lower mechanical qualities. Often the base is a biphasic calcium phosphate, which combines 40-60% TCP with 60-40% HA, yielding a more physiological balance between mechanical support and bone resorption.

Synthetic bone grafts are widely known and are proven to be safe and effective in bone substitution. HA-TCP materials are available in form of blocks, granules and injectable kits. The pore size varies between different materials but is generally within the range of 0.1 to 1000 μm, such as 100-800 μm. Pore interconnectivity is necessary for bone ingrowth. Depending on the concentration of HA and TCP, the strength is variable between 10 and 60 MP, which is lower than cortical bone compression strength (150-200 MP), which is one of the major limit of ceramic based biomaterials.

An exemplary HA-TCP material includes a porous biphasic synthetic bone-graft substitute in granulated form, herein denoted Oss. It consists of biphasic calcium phosphate, a composite of 10% hydroxyapatite and 90% β-tricalcium phosphate. The pore size is 0.1-1000 μm. The total porosity in this material is about 50-85%, such as 65±15% or 70±15%.

Another exemplary HA-TCP material is Straumann BoneCeramic® (Straumann AG, Basel, Switzerland) which is a synthetic bone-graft substitute designed for augmenting bone. It consists of biphasic calcium phosphate with a composite of 60% hydroxyapatite and 40% β-tricalcium phosphate. BoneCeramic® is 90% porous with interconnected pores of 100-500 μm in diameter.

Yet another exemplary HA-TCP material is Botiss Maxresorb® (Botiss dental GmbH, Berlin, Germany) which is a synthetic bone-graft substitute designed for augmenting bone. It consists of biphasic calcium phosphate with a composite of 60% hydroxyapatite and 40% β-tricalcium phosphate. Maxresorb® is 80% porous with interconnected pores of 200-800 μm in diameter and micropores having a diameter of 1-10 μm.

Hydroxyapatite (HA) is the primary mineral component of teeth and bone. HA ceramics come in both naturally and synthetic forms. HA and TCP ceramics are manufactured in a variety of forms including granules and porous blocks. TCP is more soluble than HA. Although HA accounts for nearly 70% of the mineral content of teeth and bone, the occurring HA in the human body exists in a substituted form. Carbonate, silicates, and magnesium among other ions, may replace hydroxyl or phosphate groups of the apatite structure. Investigators have attempted to produce HA that more closely resembles the mineral content of native bone, enhancing bioactivity and osteoconduction (Biomimetic ceramic substitutes).

Calcium Phosphate Cements

Calcium phosphate cements (CPC) are synthetic bone substitutes. The cements are a white powder, consisting of calcium phosphate, that when mixed with a liquid, forms a workable paste which can be shaped during surgery to fit the contours of bone loss. The cements harden within 20 min. The hardening reaction, which forms nanocrystalline hydroxyapatite (HA) is isothermic and occurs at physiologic pH so tissue damage does not occur during the setting reaction. CPCs were FDA approved for the treatment of non-load-bearing bone defects in 1996. HA is the primary inorganic component of natural bone which makes the hardened cement biocompatible and osteoconductive. Over time, CPCs are gradually resorbed and replaced with new bone. Because CPCs are brittle, they are used for non-load-bearing applications such as dental, crania-facial and orthopedic applications. CPCs have two significant advantages over pre-formed, sintered ceramics. First, the CPCs paste can be sculpted during surgery to fit the cavities. Second, the nanocrystalline hydroxyapatite structure of the CPC makes it osteoconductive causing it to be gradually resorbed and replaced with new bone.

Recently the research on CPC has focused on improving mechanical properties, making premixed cements, making the cement macroporous and seeding cells and growth factors into the cement.

Calcium Sulphate

Calcium sulphate (CS) is resorbed variably within 6-8 weeks. Due to rapid graft resorption, the resulting calcium-rich fluid incites inflammation. Recently many adverse or no effects were reported, mainly explained because of the too fast resorption and the production of a similar inflammatory reaction without bone formation (13-18%).

Polymer-Based Bone Graft Substitutes

Polymers have physical, mechanical, and chemical properties completely different from the other bone substitutes. The polymers can be divided into natural polymers and synthetic polymers. These, in turn, can be divided further into degradable and nondegradable types.

Degradable synthetic polymers are resorbed by the body. The benefit is that they enhance healing without remaining foreign bodies. Degradable polymers such as polylactic acid and poly(lactic-co-glycolic acid) have been used as stand-alone devices and as extenders of autografts and allografts.

Composite Materials

Composite of Collagen and Hydroxyapatite

Bone is mainly made of collagen (Col) and carbonate substituted hydroxyapatite (HA). Actually it is possible to obtain Col-HA by a self-assembling process on a nanometric scale.

Thus, an implant manufactured from such components is likely to behave better than other bone substitutes made as monolithic devices. Indeed, both collagen type I and hydroxyapatite were found to enhance osteoblast differentiation, but combined together, they were shown to accelerate osteogenesis.

The direct comparison of other materials compared with Col-HA composites for bone substitutes have yet to be clearly investigated. However, increasing the biomimetic properties of an implant may reduce the problems of bacterial infections associated with inserting a foreign body.

Growth Factors

Several bone-inducing growth factors are currently known in the field of the art, such as bone morphogenetic proteins (BMP), insulin growth factor (IGF), transforming growth factor (TGF), fibroblast growth factor (FGF), able to stimulate activation and migration of osteogenic stem cells and progenitor cells, and to induce revascularization.

The challenge to tissue engineers is to design and develop temporary bone scaffolds which deliver bioactive molecules and drugs or cells to the injury site and hence extend its biological functionality (accelerate healing and tissue regeneration while simultaneously preventing pathology). Although mimicking the geometric architecture of bone in a synthetic scaffold has been shown to promote favorable cellular activity, the overall capacity for a scaffold to direct cell behavior can be substantially improved through the controlled delivery of bio specific cues. Administration of growth factors and other bioactive molecules to promote bone formation and repair has achieved promising results in several preclinical and clinical models.

The efficacy of the delivery vehicle relies on its ability to provide the appropriate dose over the appropriate therapeutic time. Ideally, the presentation of bioactive molecules or drugs must be finely tuned to dynamically match the physiological needs of the tissue as it regenerates.

Many synthetic bone scaffolds rely on the delivery of single factors, which may partially explain the limited clinical utility of many current approaches. Therefore, researchers have been investigating techniques to encapsulate and release multiple bioactive molecules in a highly controlled spatial and temporal manner. Research has shown that this method significantly enhances tissue regeneration compared with the controlled release of single biological cues. The technology of incorporating multiple chemical effectors and controlling their spatial and temporal release is a very promising strategy, but is still experimental and has not yet demonstrated widespread preclinical or clinical utility to date.

The failure to identify either a single material or growth factor as the panacea for bone regeneration, or a biological scaffold that will promote integration and vascularization, has led to an increased interest in optimizing biomaterials to promote specific cell-biomaterial interactions.

New strategies work to encapsulate and release drugs which prevent pathologies that can occur post implantation of a synthetic scaffold. A wide variety of drugs have been encapsulated and released from biodegradable polymer scaffolds including antibiotics, DNA, RNA, cathepsin inhibitors, chitin, chemotherapeutics, bisphosphonates, statins, sodium fluoride, dihydropyridine, and many others. Researchers are aggressively pursuing strategies to deliver antibiotics locally to the site of injury/surgery. Although local delivery of antibiotics has a very promising outlook, there remains a number of challenges (such as antibiotic stability within the scaffold and antibiotic deactivation during fabrication), which still need to be addressed.

Emdogain®

Recent studies conducted by the present inventors have developed a gel that is injectable by means of a syringe to the site of a bone defect, named Emdogain®. This gel consists of two components, propylene glycol alginate (PGA) and Enamel Matrix Derivative (EMD). While PGA has a structural role and acts as a carrier, EMD is the active component that favours the regeneration of the diseased periodontal tissue by mediating the formation of acellular cementum at the root of the tooth and providing a foundation for the growth of the tissue associated with functional attachment. Once the gel is applied to the site of a defect, the pH tends to strive to the physiological value and when it reaches a value of 6, it causes EMD to precipitate. Afterwards, the osteoblast and cementoblast cells are enticed by the natural cocktail of isolated enamel matrix proteins to proliferate and cause the ligament extension from the gingival wall into the intrabony gum.

Several problems still remain with this approach; even if it has been shown that PGA appears to enhance the precipitation of EMD, it might also undergo a phase separation and degradation during its storage that compromises its integrity and structural role as a carrier. EMD on its own, on the other hand, has not the structural ability to sustain the charges caused by the new regenerating tissues. In general, it is required that EMD remains stable and shows a predictable evolution of properties during its sterilization and storage. Indeed, the precipitation and loss of regenerative capacity of EMD particles prior to the application has to be avoided.

Straumann® Emdogain® is a commercially available product composed of Propylene Glycol Alginate (PGA) and porcine Enamel Matrix Derivative (EMD) proteins. The PGA employed in the manufacture of Straumann® Emdogain® has a viscosity of 50-175 mPa·s (EMD in a 2% PGA aqueous solution 22° C. (Brookfield viscosity)). The composition Straumann® EMDOGAIN® itself, displays a viscosity of 3.0 Pas (3000 mPa·s at 22° C.). Upon dissolving alginates in water, the molecules hydrate and the solution gains viscosity. The viscosity of an alginate solution depends on the concentration of alginate and the length of the alginate molecules, i.e. the number of monomer units in the chains. In general, the longer the chains, the higher the viscosity at similar concentrations. The dissolved molecules are not completely flexible; rotation around the glycosidic linkages in the G-block regions is somewhat hindered, resulting in a stiffening of the chain. Solutions of stiff macromolecules are highly viscous.

It was found that because EMD is nearly 90% composed of amelogenin, it involves hierarchical structures based on nanoscale spherical agglomerates, also called nanospheres. These are generally only marginally stable and sensitive to environmental stresses such as temperature or pH changes, which may lead to an irreversible unfolding or misfolding of the proteins. This in turn leads to the proteins forming large unfolded aggregates that are unable to carry out their function as tissue healing inducer.

Although there is ample clinical evidence for periodontal regeneration following EMD application, its low viscosity is of concern. To avoid flap collapse in treatment of periodontal defects, use of EMD with a porous interconnected scaffold may be preferable. The scaffold should allow cell migration and proliferation, but also subsequently be assimilated by the surrounding. Unfortunately, amelogenin, the main active ingredient of EMD folds into a complex tertiary conformational structure and several units need to assemble into a macrostructure for the protein to assert its biological activity. This necessitates a co-ordinated aggregation and/or agglomeration on the surface of any material that is to be bioactivated, a task that has so far been hard to achieve due to the molecules easy degradation in solution or premature fall-out into disorganised sedimentary clumps before reaching the target surface.

In the present invention, a biocompatible material, developed from a natural bone mineral of bovine origin, in one embodiment available as granules of spongious bone having a bimodal pore distribution, as well as a porous synthetic bone substitute, were for the first time successfully bioactivated with a low viscosity composition comprising EMD as is described in the following.

SUMMARY OF THE INVENTION

The present document is directed to a composition for bioactivating a bone graft material, said composition comprises isolated enamel matrix proteins at a concentration of 0.3 mg/ml-100 mg/ml in a suitable pharmaceutical carrier, said composition having a pH between pH 3.8-4.2, and a viscosity of less than 50 mPa·s at 22° C. (room temperature). The pharmaceutical carrier is preferably not propylene glycol alginate (PGA). The concentration of enamel matrix proteins in the composition may be about 29-31 mg/ml, such as about 29, 30 or 31 mg/ml. The suitable pharmaceutical carrier may e.g. be acetic acid or PBS. In a preferred embodiment, the pharmaceutical carrier is acetic acid.

The present document is also directed to the use of a composition as defined herein for bioactivating a bone graft material for improved bone regeneration.

The present document is thus also directed to a process for preparing a bioactivated bone graft material for improved bone regeneration, comprising
a) obtaining a porous bone graft material,
b) coating and/or soaking and/or filling said bone graft material with a composition comprising isolated enamel matrix proteins at a concentration of 0.3 mg/ml-100 mg/ml in a suitable pharmaceutical carrier, having a pH between pH 3.8-4.2, and a viscosity of less than 50 m Pa·s at 22° C. (RT), such as between 30-1.0 mPa·s at 22° C. (RT), and
c) optionally lyophilizing said bone graft material.

In a process for preparing a bioactivated bone graft material for improved bone regeneration as disclosed herein, the pH of the composition may be between pH 3.8-4.2 before mixing components a) and b).

The total porosity of the bone graft material may be about 70-98%, such as 70%, 75%, 80%, 85%, 90.0%, 91.2%, 92%, 93% or 95%.

In a process for preparing a bioactivated bone graft material for improved bone regeneration as disclosed herein, the composition comprising isolated enamel matrix proteins used in step b) may comprise isolated enamel matrix proteins at a concentration of about 29-31 mg/ml, such as at a concentration of about 29, 30 or 31 mg/ml.

In a process for preparing a bioactivated bone graft material for improved bone regeneration as disclosed herein, the suitable pharmaceutical carrier of the composition comprising isolated enamel matrix proteins used in step b) may e.g. be acetic acid or PBS.

The bone graft material may e.g. be selected from the group consisting of natural bone, synthetic bone and scaffolds, such as natural bone and synthetic bone material.

The present document is also directed to a bioactivated bone graft material for improved bone regeneration which is prepared using a process comprising the steps of:
a) obtaining a porous bone graft material,
b) coating and/or soaking and/or filling said bone graft material with a composition comprising isolated enamel matrix proteins at a concentration of 0.3 mg/ml-100 mg/ml in a suitable pharmaceutical carrier, having a pH between pH 3.8-4.2, and a viscosity of less than 50 m Pa·s at 22° C. (RT), such as between 30-1.0 mPa·s at 22° C. (RT), and
c) optionally lyophilizing said bone graft material,
wherein at least 50-90% of the isolated enamel matrix proteins comprised in and/or on the bioactivated bone graft material are assembled amelogenin nanospheres, which precipitate in a main peak centered around 1500 nm, as measured by DLS.

The present document is also directed to bioactivated porous bone graft material for improved bone regeneration, wherein at least 50-90% of the isolated enamel matrix proteins comprised in and/or on the bioactivated bone graft material are assembled amelogenin nanospheres, which precipitate in a main peak centered around 1500 nm, as measured by DLS.

The bone graft material may be selected from the group comprising a bovine xenograft and a synthetic bone graft material. The bone graft material may also be in the form of granules. Typically, the overall porosity of the bone graft material is at least 70%.

The present document is also directed to a kit for preparing a bioactivated bone graft material for improved bone regeneration as defined herein, said kit comprising at least two components; 1) a porous bone graft material, and 2) a composition comprising isolated enamel matrix proteins at a concentration of 0.3 mg/ml-100 mg/ml in a suitable pharmaceutical carrier, said composition having a pH between pH3.8-4.2, and a viscosity of less than 50 mPa·s at 22° C. (RT), such as between 30-1.0 mPa·s at 22° C. (RT).

The present document is also directed to a bioactivated bone graft material as defined herein for use in medicine.

The present document is also directed to a bioactivated bone graft material for improved bone regeneration as defined herein for use in improving bone regeneration.

The present document is also directed to the use of a composition comprising isolated enamel matrix proteins at a concentration of 0.3 mg/ml-100 mg/ml in a suitable pharmaceutical carrier, said composition having a pH between pH 3.8-4.2, and a viscosity of less than 50 m Pa·s at 22° C. (RT), such as between 30-1.0 mPa·s at 22° C. (RT) for manufacturing a bioactivated bone graft material as defined herein for improving bone regeneration.

The present document is also directed to a method for improving bone regeneration in a patient in need thereof comprising implanting a bioactivated bone graft material as defined herein.

DISCLOSURE OF THE INVENTION

The present invention for the first time discloses a low viscosity composition comprising enamel matrix derivative (EMD) which, when applied to a porous bone graft material, improves and/or enhances bioactivity and osteoconduction of said bone graft material. The present invention consequently also for the first time discloses a bioactivated bone graft material with enhanced bioactivity and/or improved osteoconduction promoting properties comprising enamel matrix derivative (EMD). As a result of said bioactivation, said bone graft material displays enhanced biocompatibility after implantation.

In one embodiment of the present invention, a kit is provided comprising a) a low viscosity composition comprising enamel matrix derivative (EMD) together with b) a porous bone graft material, to be combined immediately before the placing of the bioactivated bone graft material by the skilled practitioner. In another embodiment, a bioactivated bone graft material, soaked in and/or coated with a low viscosity composition comprising enamel matrix derivative (EMD), is provided ready for use.

In particular, bone substitutes obtained from the mineral part of bovine bone are demonstrated to fulfill both physical and biological requirements for a new, easy to apply injectable scaffold for use in combination with a low viscosity composition comprising enamel matrix derivative (EMD).

As is demonstrated in the experimental section of the present application, a biocompatible material, developed from a natural bone mineral of bovine origin (Bio-Oss®), as well as one of synthetic origin (Oss) consisting of biphasic calcium phosphate, a composite of 10% hydroxyapatite and 90% β-tricalcium phosphate, having a bimodal pore distribution, was successfully bioactivated with a low viscosity composition comprising EMD. The bioactivated scaffold material in this particular embodiment resembles the human bone, and its interconnecting pores permit the formation and ingrowth of new tissue.

The first experiments done consisted in observing the behavior and characterizing of different combinations of solutions containing EMD diluted in acetic acid and Bio-Oss®, a biocompatible material, developed from a natural bone mineral of bovine origin. Afterwards, the same experiments were performed replacing Bio-Oss® with Oss (a synthetic bone substitute material), which is another scaffold material mainly composed of hydroxyapatite/TCP granules. Parameters as the influence of time and the initial pH of the EMD solutions were investigated by fluorescence, Dynamic Light Scattering (DLS), and Scanning Electron Microscopy (SEM). These analyses permitted obtaining useful information on how the aggregation and precipitation processes evolve in time, on the size and morphology of the formed aggregates, and about their coverage on the Bio-Oss® or Oss granules.

EMD was dissolved in buffer systems at different pH, mixed with bovine bone grafts (1:1), and the pH and viscosity changes recorded. The Brunner-Emmer-Teller (BET) technique was used to measure bone graft porosity and specific surface area. EMD aggregation before and after bone graft addition was monitored by fluorescence measurements and aggregate/precipitate sizes were determined by dynamic light scattering (DLS).

Addition of bovine bone grafts to EMD solutions caused pH and viscosity increases and was clearly shown to favor EMD aggregation and precipitation (FIG. 1, top), which is the first step in the regenerative process in vivo. Addition of synthetic bone grafts to EMD solutions caused pH and viscosity increases in a similar manner albeit not as forcefully as seen with the bovine bone graft. In particular, pH 4 was identified as a critical threshold above which EMD aggregation and precipitation occurred immediately after bone graft addition, and agglomerates no longer completely covered the bone graft surface (FIG. 1, bottom). Below pH 4, precipitation was delayed, and partial unfolding of the EMD resulted in a shift in the size distribution of the aggregates to higher values. pH 4 therefore provided the best compromise in properties, the delay in EMD precipitation allowing sufficient time for application, while being short enough for the folded EMD conformation to be maintained and to ensure homogenous coverage of bone graft surface. Different aggregation rates and precipitate sizes were observed depending on the initial pH of the EMD solutions and the overall porosity of the bone graft material used. There is no reason to speculate that the actual origin of the material is of any crucial importance, but instead the favourable precipitation, aggregation and/or agglomeration seems at least in part to occur in relation to and/or be improved by the porosity of the material used.

As is shown in FIG. 1 (EMD precipitation as a function of time after bone graft addition at different initial pH (top), scanning electron micrograph of EMD precipitates at the bone graft surface at an initial pH of 4.35 (bottom)), EMD prepared at an initial pH of 4 and mixed with bovine bone grafts satisfies the biological and physical requirements of an injectable scaffold for periodontal regeneration. Under these conditions, the EMD proteins precipitate in a folded state, preserving their regenerative properties, and coat the bone graft homogeneously to give a viscous, biocompatible scaffold, with the potential to fill periodontal defects and prevent flap collapse.

DETAILED DISCLOSURE

The present invention for the first time discloses a low viscosity composition comprising enamel matrix derivative (EMD) which, when applied to a porous bone graft material, improves and/or enhances bioactivity and osteoconduction of said bone graft material.

In particular, the present invention for the first time discloses a composition for bioactivating a bone graft material, comprising isolated enamel matrix proteins at a concentration of 0.3 mg/ml-100 mg/ml in a suitable pharmaceutical carrier, said composition having a pH between pH 3.8-4.2, and a viscosity of less than 50 mPa·s at 22° C. (RT), such as between 30-1.0 mPa·s at 22° C. (RT). Said composition is in the present context used for bioactivating a porous bone graft material for improved bone regeneration.

EMD

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. Enamel matrix proteins can therefore promote periodontal regeneration through mimicking the natural attachment development in the tooth (Gestrelius S, Lyngstadaas S P, Hammarström L. Emdogain—periodontal regeneration based on biomimicry. Clin Oral Invest 4:120-125 (2000)).

Isolated enamel matrix proteins are able to induce not only one, but an orchestrated cascade of factors, naturally found in tissues developing adjacent to the enamel matrix. They mimic the natural environment of a developing tissue and thus mimic a natural stimulation for tissue regeneration, cell differentiation and/or maturation.

Enamel matrix derivative (EMD), in the form of a purified acid extract of proteins from pig enamel matrix, has previously been successfully employed to restore functional periodontal ligament, cementum and alveolar bone in patients with severe tooth attachment loss (Hammarström et al., 1997, Journal of Clinical Periodontology 24, 658-668).

Enamel Matrix Derivative (EMD) proteins and enamel matrix proteins are widely used in clinical dentistry because of their ability to promote regeneration of soft and hard tissues and to reduce inflammation and infections.

Purified Enamel Matrix Derivative (EMD) proteins contain 3 major protein fractions which are separable by High Pressure Liquid Chromatography (HPLC). These fractions are named fraction A, B and C, respectively. A typical weight ratio of the isolated and/or purified proteins is about 80/8/12 between the main protein peaks at 20, 14 and 5 kDa, respectively.

As mentioned above, the fraction C typically has a molecular weight of between approximately 3, 5 and 5 kDa, such as approximately 5 kDa, 4 kDa and 3.5 kDa, as determined by SDS PAGE electrophoresis. The fraction A typically has a molecular weight of approximately 20 kDa, as determined by SDS PAGE electrophoresis. The fraction B typically has a molecular weight of between approximately 6 kDa and 15 kDa, such as approximately 15 kDa, 12 kDa, 10 kDa and 6 kDa, as determined by SDS PAGE electrophoresis.

EMD proteins and/or enamel matrix proteins are composed of a number of proteins, such as amelogenin, enamelin, tuft protein, proteases, and albumin. Amelogenin, a major constituent of EMD proteins and/or enamel matrix proteins (up to approximately 90%), are a family of hydrophobic proteins derivable from a single gene by alternative splicing and controlled post secretory processing. They are highly conserved throughout vertebrate evolution and demonstrate a high overall level of sequence homology among all higher vertebrates examined (80%). In fact, the sequences of porcine and human amelogenin gene transcript differ only in 4% of the bases. Thus, enamel matrix proteins or EMD proteins, although of porcine origin, are considered "self" when encountered in the human body and can promote dental regeneration in humans without triggering allergic responses or other undesirable reactions.

In the present context, purified Enamel Matrix Derivative (EMD) proteins are thus defined as enamel matrix proteins comprising at least 60-70% amelogenin, such as at least 60, 61, 62, 63, 64, 65, 66, 67, 68, 69 or 70%, with a molecular weight of about 20-25 kDa, such as 20, 21, 22, 23, 24, or 25 kDa, or such as between 20-22, 20-24, or 20-23 kDa. In general, the weight ratio of the purified and/or isolated enamel matrix proteins is about 80/8/12, such as 75-85/5-12/5-15, or such as at least 80%, at least 8%, and at least 5%, between the main protein peaks of fraction A, B and C, respectively. Approximately 60-90%, such as at least 60, 61, 62, 63, 64, 65, 66, 67, 68, 69, 70, 80, 70-90, 60-70, 70-80, or 80-90% of the purified and/or isolated enamel matrix proteins are amelogenin and/or fragments or derivatives of amelogenin.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Another preferred example is Clustal W (http://www.ebi.ac.uk/clustalw/). Each sequence analysis program has a default scoring matrix and default gap penalties. In general, a molecular biologist would be expected to use the default settings established by the software program used.

The amino acids in an EMD protein and/or enamel matrix protein may further be modified in terms of chemistry, isometry or in any other way as long as the sequences of the protein is intact. Modifications of the amino acids of the EMD protein and/or enamel matrix protein may increase the activity, stability, biocompatibility or clinical performance of the proteins, or reduce toxicity and adverse reactions to the proteins. Examples of chemical modifications include, but are not limited to, glycosylation and methylation. The amino acids may also be of all different types of stereoisomeric forms, such as D or L forms of amino acids, or S or R isomers. The amino acids in an EMD protein and/or enamel matrix protein of the invention may also be replaced by synthetic analogues thereof. The use of synthetic analogues may e.g. result in an EMD protein and/or enamel matrix protein that is more stable and less prone to degradation. Examples of unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-l-phenylalanine*, L-allyl-glycine*, ß-alanine*, L-a-amino butyric acid*, L-g-amino butyric acid*, L-a-amino isobutyric acid*, L-e-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * is herein utilised to indicate the hydrophobic nature of the derivative whereas # is utilised to indicate the hydrophilic nature of the derivative, #* indicates amphipathic characteristics.

EMD proteins and/or enamel matrix proteins may further comprise N- and/or C-terminal tags comprising the amino acids His and/or Met.

In one embodiment, the EMD proteins and/or enamel matrix proteins are produced instead of isolated from a natural source, e.g. by synthetic production or biosynthesis. The EMD proteins and/or enamel matrix proteins, or fragments thereof may be produced by any known method for production of peptides, such as synthetic production by chemical synthesis. Synthetic production also allows the use of amino acid analogues which may improve the stability of the proteins or fragments produced. The skilled person knows the methods that are available for the synthesis of an amino acid sequence.

Preferably, bioproduction may be used as a method for producing the EMD proteins and/or enamel matrix proteins, or fragments thereof. Bioproduction means the production of an amino acid sequence in a biological system, such as a cell culture or in microbial cells, e.g. bacterial cells.

The present invention relates to a composition comprising enamel matrix proteins and/or enamel matrix derivative (EMD) proteins, wherein at least 60-70%, such as 60, 61, 62, 63, 64, 65, 66, 67, 68, 69 or 70%, of the proteins have a molecular weight between 16-40 kDa, such as above 20 kDa, such as 16, 17, 18 or 19 kDa.

The composition comprising isolated enamel matrix proteins used in step b) of the process described in the present invention comprises isolated enamel matrix proteins at a concentration of 0.01 to 100 mg/ml, such as of 0.3 mg/ml-100 mg/ml, or of 29-31 mg/ml, such as at a concentration of 29, 30 or 31 mg/ml. In one embodiment, the concentration of the EMD proteins and/or enamel matrix proteins in a composition according to the invention is around 29 mg/ml.

When EMD proteins and/or enamel matrix proteins are applied to the porous bone graft material in a composition according to the present invention, comprising isolated enamel matrix proteins at a concentration of 0.3 mg/ml-100 mg/ml in a suitable pharmaceutical carrier, said composition having a pH between pH 3.8-4.2, and a viscosity of less than 50 m Pas at 22° C. (RT), such as between 30-1.0 mPa·s at 22° C. (RT), the EMD proteins and/or enamel matrix proteins precipitate in a folded state, preserving their regenerative properties, and coat the bone graft homogeneously to give a viscous, biocompatible scaffold, with the potential to fill periodontal defects and prevent flap collapse.

Suitable Pharmaceutical Carrier

The composition may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

In the present context, pharmaceutically or cosmetically acceptable excipient, carrier and/or diluent is a substance which is substantially harmless to the individual to which the formulation is to be administered. Such an excipient, carrier and/or diluent normally fulfills the requirements given by the national health authorities. Official pharmacopoeias such as e.g. the British Pharmacopoeia, the United States of America Pharmacopoeia and The European Pharmacopoeia set standards for pharmaceutically acceptable excipients.

The suitable pharmaceutical carrier of the present invention may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of buffering agents are e.g. citric acid, acetic acid, tartaric acid, lactic acid, hydrogenphosphoric acid, etc.

In one embodiment, the suitable pharmaceutical carrier of the composition comprising isolated enamel matrix proteins is to be selected from the group consisting of acetic acid and PBS. In a presently preferred embodiment, the suitable pharmaceutical carrier of the composition comprising isolated enamel matrix proteins is acetic acid.

Preferably, the carrier does not comprise or consist of propylene glycol alginate (PGA).

In one embodiment, the composition of the present invention comprising isolated enamel matrix proteins may further include arginine. In particular in a concentration range of 700 mM or lower, such as 10-700 mM, 100-700 mM or 200-700 mM is preferred, in particular when the concentration of EMD is at least 20 mg/ml, such as about 29-31 mg/ml, such as about 31 mg/ml.

pH

Different aggregation rates and precipitation sizes depend at least partially on the initial pH of the composition.

Addition of bovine bone grafts and synthetic bone grafts to EMD solutions causes pH and viscosity increases and is clearly shown to favor correct EMD aggregation and precipitation.

In particular, a range of pH between pH 3.8-4.2 and in particular pH 4 is identified as a critical threshold above which EMD aggregation and precipitation occurs immediately after bone graft addition, and agglomerates no longer completely cover the bone graft surface. Below pH 4, precipitation is delayed, and partial unfolding of the EMD results in a shift in the size distribution of the aggregates to higher values. pH 4 therefore provides the best compromise in properties, the delay in EMD precipitation allowing sufficient time for application, while being short enough for the folded EMD conformation to be maintained and to ensure homogenous coverage of bone graft surface.

Different aggregation rates and precipitate sizes depend on the initial pH of the EMD solutions and the overall (total) porosity of the bone graft material used.

Thus, the present invention provides for a composition for bioactivating a bone graft material, comprising isolated enamel matrix proteins at a concentration of 0.3 mg/ml-100 mg/ml in a suitable pharmaceutical carrier, said composition having a viscosity of less than 50 m Pa·s at 22° C. (RT), such as between 30-1.0 mPa·s at 22° C. (RT) and a pH between pH 3.8-4.2, such as selected from the group consisting of a pH between 3.8-4-1, 3.8-4.0, 3.8-3.9, 3.9-4.2, 3.9-4.1, 3.9-4.0, 4.0-4.1, 4.0-4.2, and 4.1-4.2.

In one embodiment, said composition for bioactivating a bone graft material, comprising isolated enamel matrix proteins has a pH of 3.8, 3.9, 4.0, 4.1 or 4.2.

The present invention also provides for a use of a composition comprising isolated enamel matrix proteins at a concentration of 0.3 mg/ml-100 mg/ml in a suitable pharmaceutical carrier, for bioactivating a bone graft material for improved bone regeneration, said composition having a viscosity of less than 50 m Pa·s at 22° C. (RT), such as between 30-1.0 mPa·s at 22° C. (RT) and a pH between pH 3.8-4.2.

In one embodiment of said process for preparing a bioactivated bone graft material for improved bone regeneration, the pH of the composition is between pH3.8-4.2 before mixing components a) and b).

Viscosity

Different aggregation rates and precipitation sizes depend at least partially on the initial viscosity of the composition.

A bone graft is a porous material. Thus, the surface of a given bone graft is in general distributed throughout the bone graft, as well as at the periphery of the graft. A suitably low viscosity therefore allows for EMD (amelogenin) aggregation, precipitation and/or agglomeration to occur on the complete bone graft surface and not only on the peripheral surfaces of the graft. This ensures homogenous coverage of a given bone graft surface.

The present invention relates to a low viscosity composition comprising isolated enamel matrix proteins. In particular, a low viscosity composition is described comprising isolated enamel matrix proteins at a concentration of 0.3 mg/ml-100 mg/ml in a suitable pharmaceutical carrier, said composition having a pH between pH 3.8-4.2.

As is clearly shown in experiment 2 of the present application, the low viscosity composition according to the present invention has a viscosity that is substantially lower than the viscosity of the commercially available of EMD formulated in PGA, which is well known to be 3000 Pa·s at 22° C., comprising EMD in a 2% aqueous solution of PGA with a viscosity between 50-175 mPa·s at 22° C. (RT). The low viscosity composition according to the present invention typically has a viscosity of less than 50 mPa·s (EMD in an aqueous solution at 22° C.), such as less than 50, 40, 30, 20, 10, 5, 2, 1.9, 1.8, 1.7, 1.6, 1.5, 1.4, 1.3, 1.2, or 1.1 mPa·s at 22° C. (RT).

The low viscosity composition according to the present invention typically has a viscosity selected from the group consisting of 50-1.0 mPa·s at 22° C. (RT), 50-10 mPa·s at 22° C. (RT), 50-1.7 mPa·s at 22° C. (RT), 30-10 mPa·s at 22° C. (RT), 30-1.7 mPa·s at 22° C. (RT), 30-1.0 mPa·s at 22° C. (RT), 10-2 mPa·s at 22° C. (RT), 10-1.7 mPa·s at 22° C. (RT), 10-1.0 mPa·s at 22° C. (RT), 5-1.7 mPa·s at 22° C. (RT), 2.5-1.2 mPa·s at 22° C., 2-1.0 mPa·s at 22° C. (RT) and 1.8-1.0 mPa·s at 22° C. (RT), such as at the most 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1.9, 1.8, 1.7, 1.6, 1.5, 1.4, 1.3, 1.2, 1.1 or 1.0 mPa·s at 22° C. (RT).

In one embodiment, the low viscosity composition according to the present invention has a viscosity that is particularly suitable for bioactivating a bone substitute with an overall porosity of at least 70%, i.e. a viscosity which is no more than 1.8 mPa·s at 22° C., such as no more than 1.7 mPa·s at 22° C., such as no more than 1.6 mPa·s at 22° C., such as no more than 1.5 mPa·s at 22° C., such as no more than 1.4 mPa·s at 22° C., such as no more than 1.3 mPa·s at 22° C., such as no more than 1.2 mPa·s at 22° C., such as no more than 1.1 mPa·s at 22° C., or such as no more than 1.0 mPa·s at 22° C., said composition comprising isolated enamel matrix proteins at a concentration of approximately 28-31 mg/ml in acetic acid and said composition having a pH between pH 3.8-4.2.

A typical low viscosity composition of the present invention, suitable for bioactivating a bone substitute with an overall porosity of at least 70%, has a viscosity of no more than 1.7 mPa·s at 22° C., comprises isolated enamel matrix proteins at a concentration of approximately 30 mg/ml in acetic acid and has a pH 4.0.

Presently preferred is a low viscosity composition of the present invention, suitable for bioactivating a bone substitute with an overall porosity of at least 70%, which comprises isolated enamel matrix proteins at a concentration of approximately 30 mg/ml in acetic acid and has a pH 4.0 and a viscosity between 2.5-1.2 mPa·s at 22° C.

The low viscosity composition according to the present invention is a composition for bioactivating a bone graft material, said composition comprises isolated enamel matrix proteins at a concentration of approximately 28-31 mg/ml in acetic acid, said composition having a pH between pH 3.8-4.2, and a viscosity of at the most 1.7 times the viscosity of water (measured as relative viscosity of liquids). With a given water viscosity of 0.9548 cp, the viscosity of said composition is 1.7 cp or less, such as 1.6 cp, 1.5 cp, 1.4 cp, 1.3 cp, 1.2 cp, 1.1 cp or less.

The substantially lower viscosity of the present composition comprising isolated enamel matrix proteins enables the composition to soak, coat and/or penetrate the porous bone graft material. Furthermore, the low viscosity of the composition comprising EMD favors amelogenin to precipitate and/or to agglomerate in a correct and/or coordinated fashion once it is applied onto or into the bone graft material.

In general, addition of bovine bone grafts and/or synthetic bone graft material, such as synthetic bone grafts, to a composition comprising isolated enamel matrix proteins in solution causes a pH increase and viscosity increase, which is shown to favor correct EMD aggregation and precipitation.

A low viscosity composition according to the present invention can further be characterized by a shear rate ($s^{-1}$) which is 0.001-500.

Amelogenin Assembly on the Graft

The present invention relates to a bioactivated bone graft material for improved bone regeneration which is prepared using a low viscosity composition comprising isolated enamel matrix proteins at a concentration of 0.3 mg/ml-100 mg/ml in a suitable pharmaceutical carrier, said composition having a pH between pH 3.8-4.2, and a viscosity of less than 50 m Pa·s at 22° C. (RT), such as between 30-1.0 mPa·s at 22° C. (RT). In and/or on the surface of said bioactivated bone graft material at least 50-90% of the isolated enamel matrix proteins are assembled nanospheres, which precipitate in a main peak centered around 1500 nm, as measured by DLS.

Aggregation, herein used exchangeable with protein aggregation, is a biological phenomenon in which proteins aggregate (i.e., accumulate and clump together) either intra- or extracellularly.

After synthesis, proteins typically fold into a particular three-dimensional conformation: their native state. Only in their native state are they functional. This folding process is driven by the hydrophobic effect: a tendency for hydrophobic portions of the protein to shield itself from the hydrophilic interior of the cell by burying into the interior of the protein. Thus, the exterior of a protein is typically hydrophilic, whereas the interior is typically hydrophobic.

However, newly synthesized proteins may not fold correctly, or properly folded proteins can spontaneously misfold. In these cases, if the cell does not assist the protein in re-folding, or degrades the unfolded protein, the unfolded protein may aggregate in a wrong conformation. In this process, exposed hydrophobic portions of the unfolded protein may interact with the exposed hydrophobic patches of other unfolded proteins, spontaneously leading to unwanted protein aggregation.

Protein aggregation can occur at all steps in the manufacturing process (cell culture, purification and formulation), storage, distribution and handling of products. It results from various kinds of stress such as agitation and exposure to extremes of pH, temperature, ionic strength, or various interfaces (e.g. air-liquid interface). High protein concentrations (as in the case of some monoclonal antibody formulations) can further increase the likelihood of aggregation.

A wide variety of aggregates are encountered in biopharmaceutical samples ranging in size and characteristics (e.g. soluble or insoluble, covalent or non-covalent, reversible or irreversible). Protein aggregates span a broad size range, from small oligomers (nanometers) to insoluble micron-sized aggregates that can contain millions of monomer units.

Aggregation needs to be carefully characterized and controlled during development, manufacture and subsequent storage of a formulated product. Similarly, by monitoring the state of aggregation, modification or optimization of the production process can be achieved.

Agglomeration is in the present context used to describe the process of smaller particles coming together and forming a larger whole.

The term precipitation is herein used interchangeably with protein precipitation and describes the creation of a solid in a solution or inside another solid during a chemical reaction or by diffusion in a solid.

In the present context, controlled aggregation and/or precipitation of enamel matrix proteins into correctly folded proteins having a biologically active conformation, as well as correct agglomeration of the isolated enamel matrix proteins into a biologically active macrostructure is achieved in a controlled manner on at least parts of the surface of a porous bone graft material, when a porous bone graft material according to the present invention is brought into contact with a low viscosity composition according to the present invention comprising the isolated enamel matrix proteins.

Bone Graft Material/Porosity

The present invention consequently discloses a bioactivated bone graft material with enhanced bioactivity and/or improved osteoconduction promoting properties. As a result of said bioactivation, said bone graft material displays enhanced biocompatibility after implantation. Thus, the present invention provides for a bioactivated porous autologous graft, allograft, xenograft, and/or synthetic graft, comprising isolated enamel matrix proteins.

In the present invention, the term "bone graft" is used to describe autologous grafts, allografts, xenografts, or synthetic grafts with similar mechanical properties to bone. Factors of importance for the biological behavior of a bone graft material include both physical and chemical factors. Physical factors of importance include form (particulate or bulk), porosity (density, pore size), surface area, surface charge and/or surface hydrophilicity, and crystallinity (crystal size, crystal perfection, and grain size). Chemical factors include composition and ionic substitution in the material, while the biological factors include local declines of the pH, degree of bone contact, type of bone, species, age, gender, hormone levels, genetic predisposition etc. Importantly, the bone graft material should mimic the properties of natural bone in order to allow for a successful integration after implantation, e.g. in terms of how amelogenin binds to bone in vivo.

For example, bone substitutes obtained from the mineral part of bovine bone are demonstrated to fulfill both physical and biological requirements for a new, easy to apply injectable scaffold for use in combination with a low viscosity composition comprising enamel matrix derivative (EMD). On the other hand, irrespective of the origin of the bone graft material, either natural or synthetic, one factor that affects the agglomeration of amelogenin onto the surface of the material is the over-all porosity of the material, i.e. the total porosity including all kinds of pores, such as macro, micro and nano pores. Different aggregation rates and precipitate sizes depend on the initial pH of the EMD solutions, it's viscosity and the total porosity of the bone graft material used.

In the range of pH between pH 3.8-4.2 and a suitable porosity of the bone graft material, in combination with a suitable viscosity of the composition, isolated enamel matrix protein aggregation and precipitation occurs in a window of time after bone graft addition, allowing for agglomerates of enamel matrix proteins, such as amelogenins, to homogenously cover at least parts of the bone graft surface, preferably the complete surface of the bone graft. In general, the practitioner must be allowed a certain delay in EMD precipitation allowing for sufficient time for application, while being short enough for the folded EMD conformation to be maintained and to ensure homogenous coverage of bone graft surface.

In one embodiment of the present invention, sufficient aggregation and/or precipitation and agglomeration of enamel matrix proteins, such as amelogenins on at least parts of the bone graft surface is achieved after 5-120 minutes, such as after 5-60 minutes, 10-30 minutes, 5-30 minutes, or 15-60 minutes. In one embodiment, sufficient aggregation and/or precipitation and agglomeration of enamel matrix proteins, such as amelogenins on at least parts of the bone graft surface is achieved no later than 120 minutes after bringing the bone graft and the composition according to the present invention into contact, such as no later than 5, 10, 15, 20, 25, 30, 45, 60, 90 or 120 minutes thereafter.

In the present context, the term "bioactivating" encompasses enhancing bioactivity and improving osteoconduction of a bone graft material. In concurrence, a bioactivated bone graft material is a bone graft material with enhanced bioactivity and/or improved osteoconduction promoting properties. As a result of said bioactivation, said bone graft material will display enhanced biocompatibility after implantation.

The bone graft material being bioactivated in a process as disclosed in the present document is selected from the group consisting of natural bone, synthetic bone and scaffolds. In one embodiment, the bone graft material being bioactivated in a process as disclosed in the present is a bovine based xenograft, such as BioOss. In another embodiment, the bone graft material is natural bone. In another embodiment the bone graft material is synthetic.

The present invention is based on the surprising finding that stable and continuous aggregation of EMD and in particular formation of amelogenin aggregates, precipitates and/or agglomerates is dependent not only on the pH and viscosity of the EMD containing composition, but also depends on the porosity of the bone graft material in itself. As can be seen in the experimental section, both Bio-Oss® and Oss permit a stable and continuous aggregation of EMD, even if this effect is more pronounced for Bio-Oss. This may be due to the lower porosity of Oss, leading to the EMD particles, which do adsorb and are integrated by the scaffold granules in the experimental set-up, do so at a lesser speed.

In general, porosity is defined by density and pore size of a given bone graft material.

The size and the interconnectivity of the pores in bone graft materials are critical factors for a successful clinical outcome. These properties influence diffusion of nutrients and oxygen, attachment, migration, and differentiation of cells, and tissue ingrowth, which are crucial steps in bone augmentation. In general, two types of pores have to be distinguished: 1) macropores (diameter>100 µm) which confer osteoconductive properties on bone substitutes and favor cell colonization; it has even been proposed that the influence of the macropore size is greater than that of macroporosity percentage, 2) micropores (diameter<100 µm) which are important for the penetration and adhesion of macromolecules and tissue fluids.

The total volume of all kinds of pores present in a material, such as the nano-, micro- and macropores, defines the total porosity.

In the present invention, it was found that a xenogenic bone substitute material made from bovine bone and consisting of small and compact natural apatite crystals has a particularly high capacity to be bioactivated with a low viscosity composition comprising EMD. Such a preferred bone graft material has a structure similar to the bone it is prepared from.

Thus, the bone graft material to be bioactivated or the bioactivated bone graft material is a bone graft material that has a total porosity of about 70-98%, such as about 70%, 75%, 80%, 85%, 90.0%, 91.2%, 92%, 93% or 95%, such as at least 70%, 75%, 80%, 85%, 90.0%, 91.2%, 92%, 93% or 95%

The average pore size of a preferred bone graft material to be bioactivated, or of the bioactivated bone graft material according to the present invention, expressed as average pore diameter, is selected from the group consisting of pore sizes between 0.1 µm and 1000 µm, such as about 100-800 µm, 200-800 µm, 250-1000 µm, 1-10 µm and 100-500 µm.

One example of a bone graft materials suitable for use in accordance with the present document include, but is not limited to, the porous biphasic synthetic bone-graft substitute in granulated form, denoted Oss, consisting of biphasic calcium phosphate, a composite of 10% hydroxyapatite and 90% β-tricalcium phosphate. The pore size is 0.1-1000 µm. The total porosity in this material is about 50-85%, such as 65±15% or 70±15%.

Another example of a suitable bone graft material is Straumann BoneCeramic® (Straumann AG, Basel, Switzerland), which a synthetic bone-graft substitute designed for augmenting bone consisting of biphasic calcium phosphate with a composite of 60% hydroxyapatite and 40% β-tricalcium phosphate. BoneCeramic® is 90% porous with interconnected pores of 100-500 µm in diameter.

Yet an example of a suitable bone graft material is Botiss Maxresorb® (Botiss dental GmbH, Berlin, Germany) which is a synthetic bone-graft substitute designed for augmenting bone. It consists of biphasic calcium phosphate with a composite of 60% hydroxyapatite and 40% β-tricalcium phosphate. Maxresorb® is 80% porous with interconnected pores of 200-800 µm in diameter; micropores have a diameter of 1-10 µm.

A further example of a suitable bone graft material are xenogenic hydroxyapatite particles (BioOss®, Geistlich Biomaterials, Wolhusen, Switzerland), a natural product of bovine origin, which is deproteinized and sintered. The total porosity of this material is 70-75% with a particle size of 250-1000 µm.

Process for Producing

A process is disclosed for preparing a bioactivated bone graft material for improved bone regeneration, comprising obtaining a porous bone graft material, coating and/or soaking and/or filling said bone graft material with a composition comprising isolated enamel matrix proteins at a concentration of 0.3 mg/ml-100 mg/ml in a suitable pharmaceutical carrier, having a pH between pH 3.8-4.2, and a viscosity of less than 50 m Pa·s at 22° C. (RT), such as between 30-1.0 mPa·s at 22° C. (RT), and optionally lyophilizing said bioactivated bone graft material.

A Kit

In one embodiment of the present invention, a kit is provided comprising a) a low viscosity composition comprising enamel matrix derivative (EMD) together with b) a porous bone graft material, to be combined immediately before the placing of the bioactivated bone graft material by the skilled practitioner. In another, equally preferred embodiment, a bioactivated bone graft material, soaked in and/or coated with a low viscosity composition comprising enamel matrix derivative (EMD), is provided ready for use.

A kit is provided for preparing a bioactivated bone graft material for improved bone regeneration, comprising at least two components;
- a. a porous bone graft material, and
- b. a composition comprising isolated enamel matrix proteins at a concentration of 0.3 mg/ml-100 mg/ml in a suitable pharmaceutical carrier, said composition having a pH between pH 3.8-4.2, and a viscosity of less than 50 m Pas at 22° C. (RT), such as between 30-1.0 mPa·s at 22° C. (RT).

Uses

In general, a bioactivated bone graft material according to according to the present invention can be used in medicine.

In particular, the present invention discloses a bioactivated bone graft material according to the present invention for use in improving bone regeneration.

In consequence, the present invention further relates to the use of a composition comprising isolated enamel matrix proteins at a concentration of 0.3 mg/ml-100 mg/ml in a suitable pharmaceutical carrier, said composition having a pH between pH 3.8-4.2, and a viscosity of less than 50 m Pa·s at 22° C. (RT), such as between 30-1.0 mPa·s at 22° C. (RT) for manufacturing a bioactivated bone graft material according to the present invention for improving bone regeneration.

Also envisioned is a method for improving bone regeneration in a patient in need thereof comprising implanting a bioactivated bone graft material according to the present invention into a patient in need thereof.

The invention is further illustrated by the following, non-limiting examples.

LEGENDS TO FIGURES

FIG. 1.

Addition of bovine bone grafts to EMD solutions caused pH and viscosity increases and was clearly shown to favor EMD aggregation and precipitation (FIG. 1, top), which is the first step in the regenerative process in vivo. However, different aggregation rates and precipitate sizes were observed depending on the initial pH of the EMD solutions. In particular, pH 4 was identified as a critical threshold above which EMD aggregation and precipitation occurred immediately after bone graft addition, and agglomerates no longer completely covered the bone graft surface (FIG. 1, bottom).

FIG. 2.

pH evolution of EMD and Bio-Oss® samples at different initial pH with and without arginine.

FIG. 3.

Fluorescence intensity of EMD in acetic acid with and without Bio-Oss® at different pH.

FIG. 4.

Fluorescence intensity of EMD in acetic acid and arginine with and without Bio-Oss® at different pH.

FIG. 5.

DLS graph of EMD in acetic acid at different pH with and without arginine.

FIG. 6.

DLS graph of EMD at pH 4.27 with different additives.

FIG. 7.

DLS graph of EMD at pH 3.87 with different additives.

FIG. 8.

DLS graph of EMD and Bio-Oss® samples with and without arginine.

FIG. 9.

SEM image of Bio-Oss® granules and EMD aggregates.

FIG. 10.

pH evolution of EMD and Oss samples at different initial pH with and without arginine.

FIG. 11.

Fluorescence intensity of EMD in acetic acid with and without Oss at different pH.

FIG. 12.

Fluorescence intensity of EMD in acetic acid and arginine with and without Oss at different pH.

FIG. 13.

DLS graph of EMD in acetic acid with Oss at different pH.

FIG. 14.

SEM image of Oss granules after EMD precipitation.

EXPERIMENTAL SECTION

Experiment 1:

Material and Methods

1. Method 1.1 Samples preparation

As the same experiments hereafter were conducted on Bio-Oss® and repeated again after replacing it with Oss, the description of the applied method is valid for both scaffold materials.

At the very beginning, four EMD and acetic acid solutions at concentration 31 mg/mL and pH 4.3, 4, 3.8, and 3.4, were prepared. Nevertheless, because the pH has a tendency to decrease in time during storage, it has been measured again before each sample production. The results were pH of 4.27, 3.87, 3.68, and 3.40 for Bio-Oss®, and pH 4.41, 3.93, 3.76, 3.31 for Oss. Afterwards, the following series of samples were prepared.

- 4 times 50 µL of EMD in acetic acid and 5 mL of Ultrapur water at initial pH 4.27, 3.87, 3.68, 3.40.
- 4 times 50 µL of EMD in acetic acid mixed with arginine (at a ratio 0.174 g for 2 mL of EMD) and 5 mL of Ultrapur water at initial pH 4.27, 3.87, 3.68, 3.40.
- 4 times 50 µL of EMD in acetic acid, added to 50 mg of Bio-Oss® and 5 mL of Ultrapur water at initial pH 4.27, 3.87, 3.68, 3.40.
- 4 times 50 µL of EMD in acetic acid added to 50 mg of Bio-Oss® and arginine (at a ratio 0.174 g for 2 mL of EMD) at initial pH 4.27, 3.87, 3.68, 3.40.

The same proportions were used again to prepare the solutions of Oss with initial pH 4.41, 3.93, 3.76, and 3.31.

Bio-Oss® is purchased from Geistlich Biomaterials, and it consists of granules having diameters of 0.25 to 1 mm. On the other hand, Oss is mainly constituted by hydroxyapatite grains of the same size range. The respected ratio of Bio-Oss® or Oss was 1 mg for 1 µL of EMD.

1.2 Specific Preparation and Apparatus 1.2.1 Fluorescence

In order to prepare the different samples for the fluorescence intensity measurement, the selected ProteoStat R Protein Aggregation Assay by Enzo has been mixed with the specific dye and Ultrapur water in the following proportions: 10 μL Dye+20 μL Assay+170 μL H20. After putting 2 μL of this solution and 100 μL of EMD at a concentration of 31 mg/mL in each recipient, also 100 mg of Bio-Oss® were added in half of the cases. At the beginning of the measurements, parameters related to the characteristics of the dye have to be entered in the program, as the excitation and emission wavelengths and bandwidths, the gain, the integration time and the number of cycles that have to be done.

1.2.2 Dynamic Light Scattering (DLS)

As only the size distribution of particles in liquid solutions can be analyzed by this technique, the supernatant was taken away from the recipients containing the granules prior to the experiment. To perform the size distribution measurement by Dynamic light scattering, it is necessary to enter some properties of the solution in the program, as the refractive and absorption index, the dielectric coefficient and the viscosity. Then, each solution has to be put individually in the sample holder before running the program, which automatically calculates how many cycles have to be performed in order to have an accurate analysis.

1.2.3 Scanning Electron Microscopy (SEM)

Initially, the Bio-Oss® or Oss granules have to be separated from the liquid solution and left to dry. Later, in order to reduce charging effects and improve the quality of the image, the samples have to be gold-coated by a process called metallization. In other words, a thin layer of gold is deposited onto the sample and will permit to evacuate the electrons of it. The estimation of the coating thickness d [Å] is given by Equation (2):

$$d = KIV t \qquad (2)$$

where K is an experimental constant (0.17 for Au), I [mA] the intensity of the current, V [kV] the voltage, and t [s] the deposition time. As the voltage was set on 1 kV and the intensity on 20 mA, for a desired coating thickness of 90 [Å], the deposition time has been of approximately thirty seconds.

2. Conclusion 2.1 Bio-Oss® Solutions 2.1.1 pH Evolution

Figure 2:
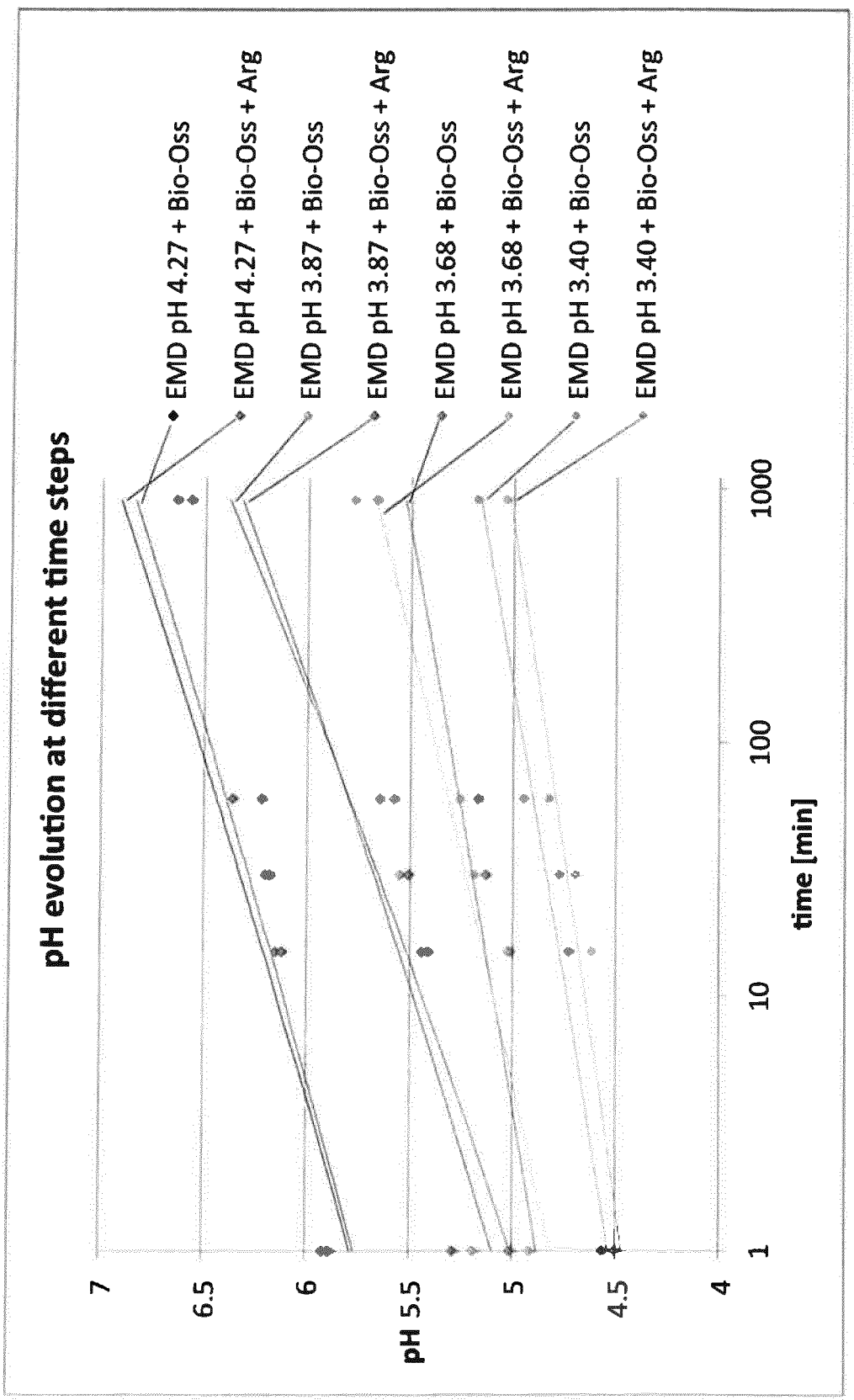

FIG. 2 shows the pH variation of solutions of EMD mixed with Bio-Oss® at initial pH 4.37, 3.87, 3.68, and 3.40 with and without arginine. It is noticeable that the samples at initial pH 4.37 reach a value of 6 in less than 10 minutes, which causes EMD precipitation due to the vicinity to the isoelectric point of amelogenin (pH 6.8). The solutions at initial pH 3.87 reach the precipitation after 200 minutes, while the two lower pH solutions precipitate only after 6 days (not presented in the graph). Whether or not arginine is added to the solutions does not seem to really influence the velocity at which the pH evolves. As the precipitation of the EMD particles has to occur within reasonable times for the application, only the solutions at initial pH 4.37 and 3.87 will be considered in the following results regarding Bio-Oss®.

2.1.2 Fluorescence

Figure 3:
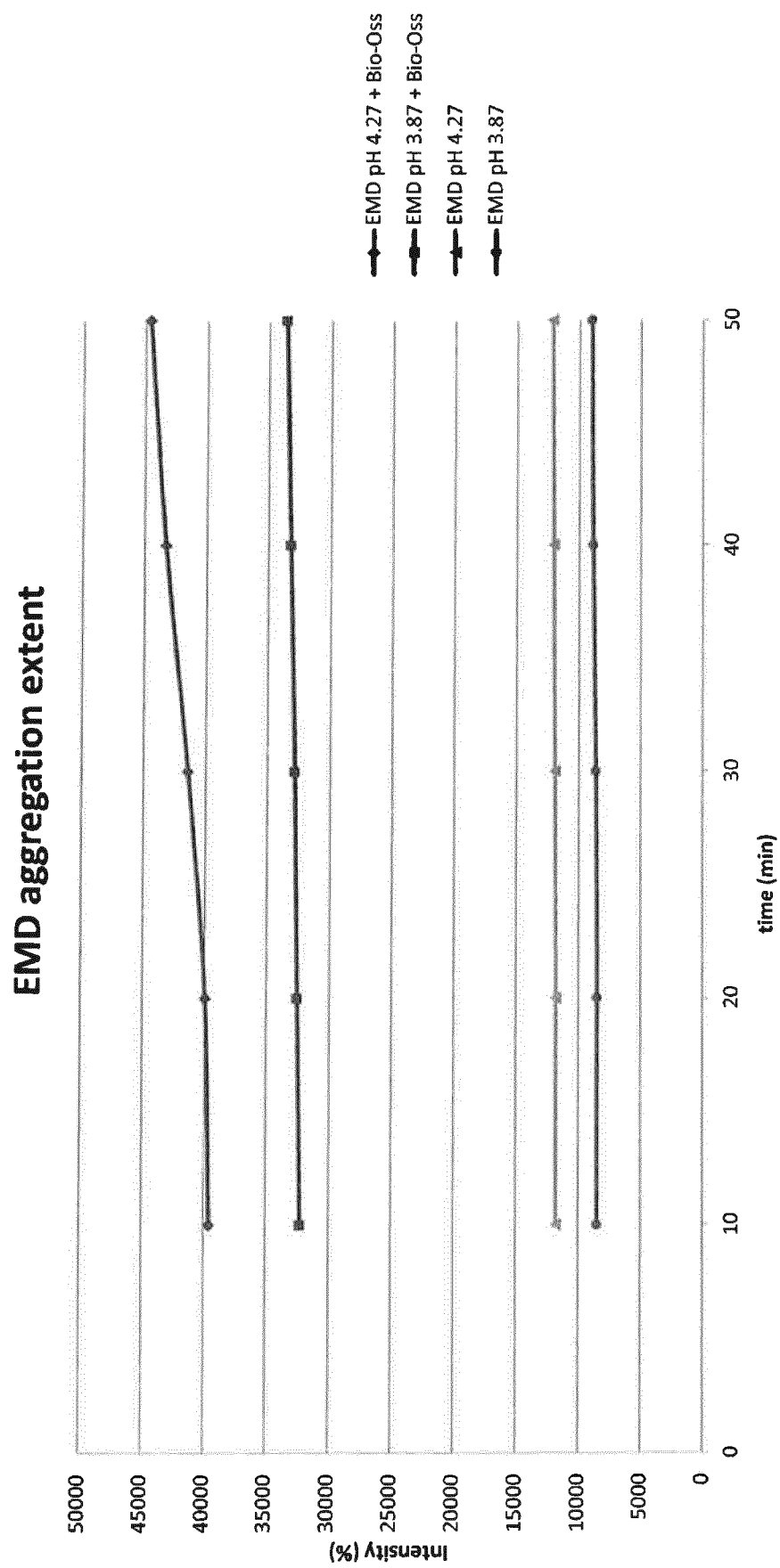

FIG. 3 shows the fluorescence intensity of EMD in acetic acid with and without Bio-Oss® at different initial pH. The solutions containing Bio-Oss® exhibit a higher intensity than the samples without it. In presence of Bio-Oss® aggregation is fast since the pH increase is favored up to precipitation, and this explains the higher intensity of the fluorescence signal. On the other hand, samples without Bio-Oss® seem not to aggregate, because there signal intensity remains constant on the overall time scale.

Figure 4:
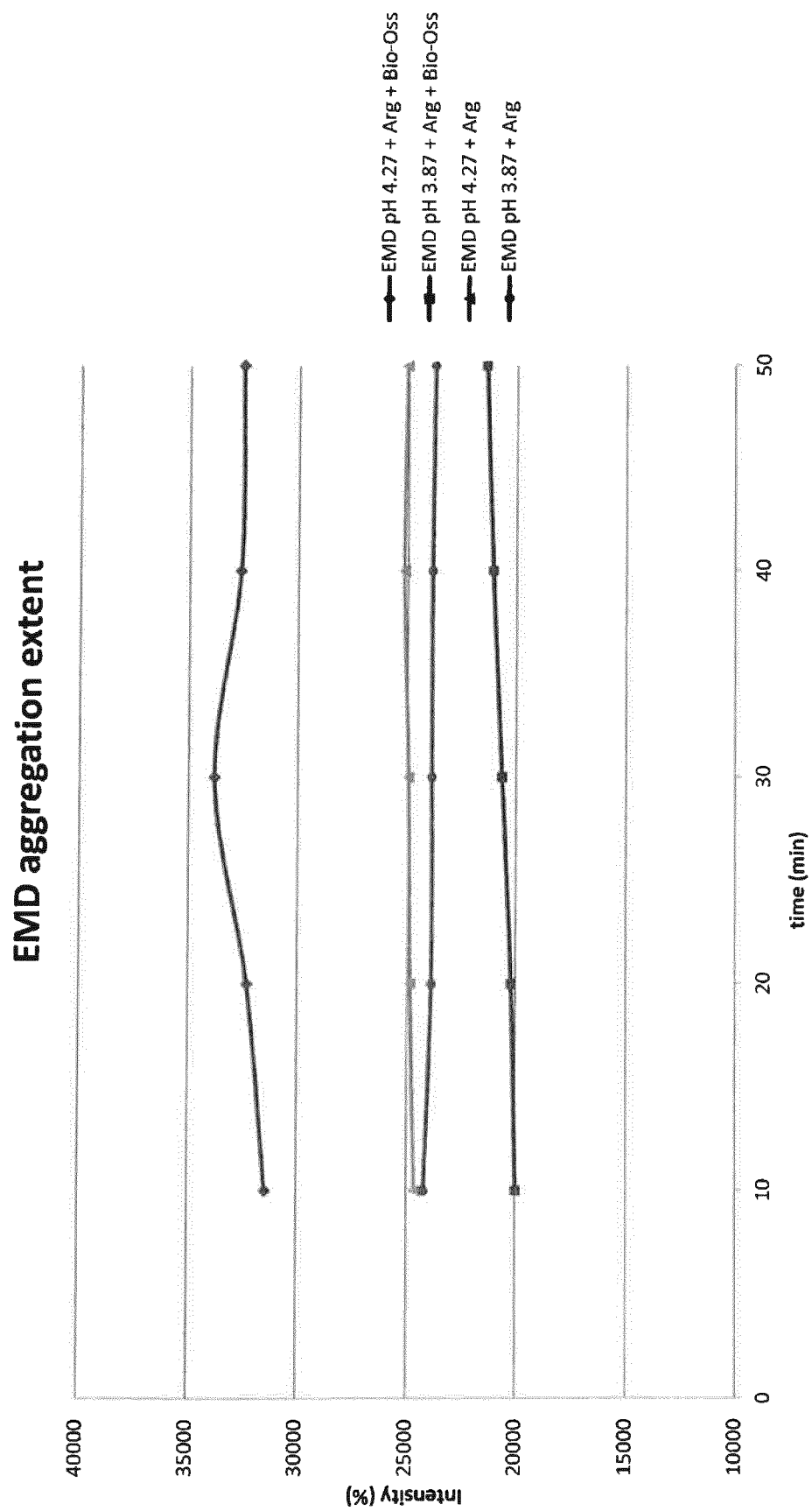

FIG. 4 shows the fluorescence intensity of EMD in acetic acid and arginine with and without Bio-Oss® at different initial pH. It is noticeable that the solution at initial pH 4.27 containing Bio-Oss® has a higher intensity than the ones without, while the solution at initial pH 3.87 has the lower signal intensity. The graph also shows that by increasing the pH of the solutions, the signal intensity raises, which means that more aggregation occurs. Compared to FIG. 3, the addition of arginine does that the signal intensity for the solutions at initial pH 4.27 and 3.87 with Bio-Oss® are decreasing. When focusing on the solutions that do not contain Bio-Oss® in FIG. 4, it can be seen that the addition of arginine has drastically increased the signal intensities compared to the samples in FIG. 3, whereas the curves corresponding to the solutions containing Bio-Oss® and arginine (FIG. 4) and only Bio-Oss (FIG. 3) are similar.

2.1.3 Dynamic Light Scattering (DLS)

Figure 5:
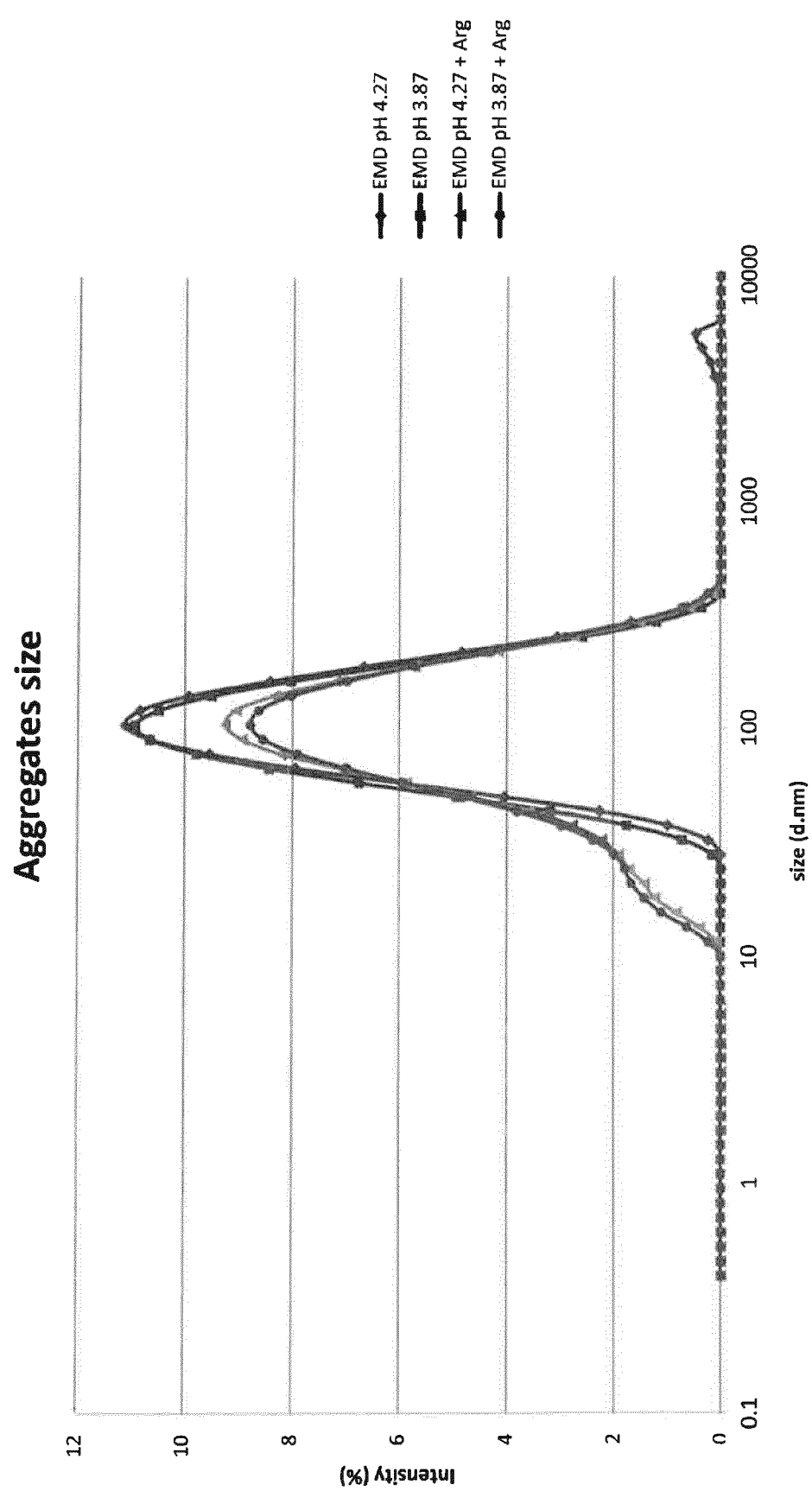

In the FIG. 5, DLS curves of EMD diluted in acetic acid samples at different pH with and without arginine are represented. The solutions without arginine have a size distribution centered around 100 nm, while the solutions containing arginine have a lower and broadened distribution that shows an extra shoulder around 30-50 nm.

Figure 6:
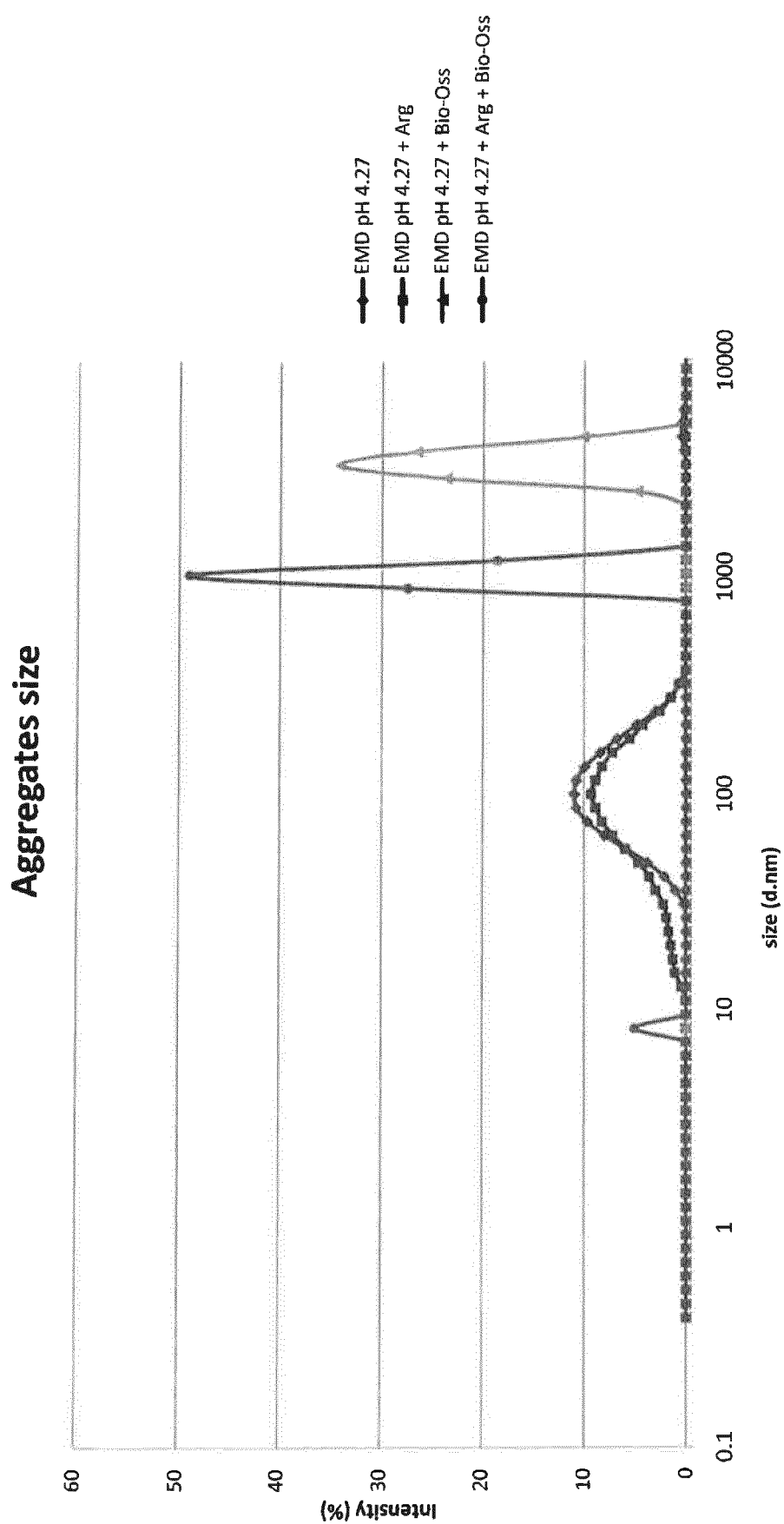

In FIG. 6 are presented the DLS graphs of EMD at pH 4.27 in acetic acid, with and without arginine and Bio-Oss®. It is noticeable that when Bio-Oss® is added to the solutions, the EMD precipitates are bigger and have a narrower and more intense size distribution. Moreover, it is observable that when arginine is added to the solution containing Bio-Oss®, the formed precipitates are smaller.

Figure 7:
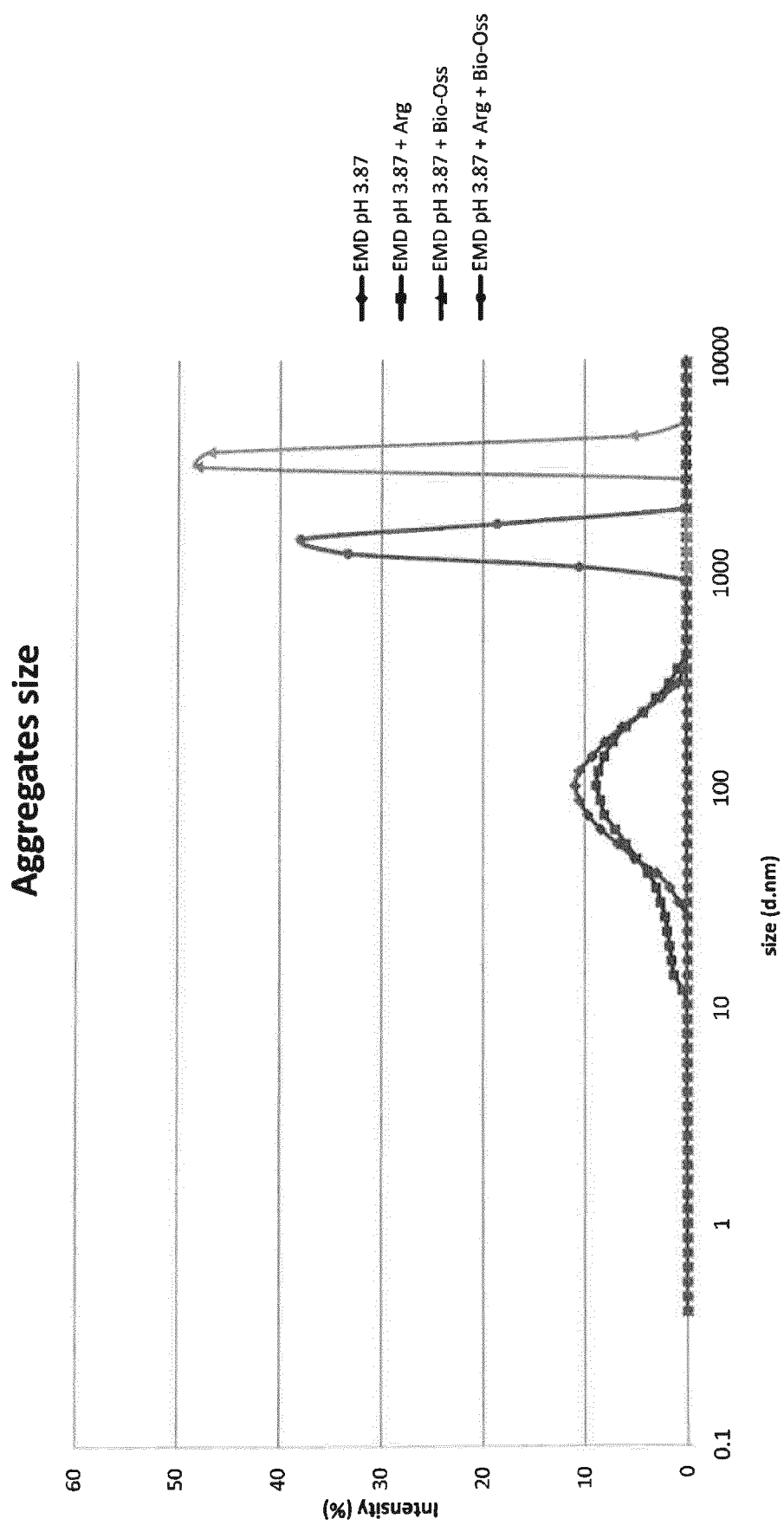

In FIG. 7 are presented the DLS graphs of EMD at pH 3.87 in acetic acid, with and without arginine and Bio-Oss®. Even if the trend of the curves in FIG. 6 is confirmed, there is an inversion in intensities between the solutions containing the scaffold. Furthermore, it must be added that at first sight, the EMD in acetic acid and EMD in acetic acid and arginine curves at pH 3.87 and 4.27 seem similar, but they are slightly different (FIGS. 6 and 7).

Figure 8:
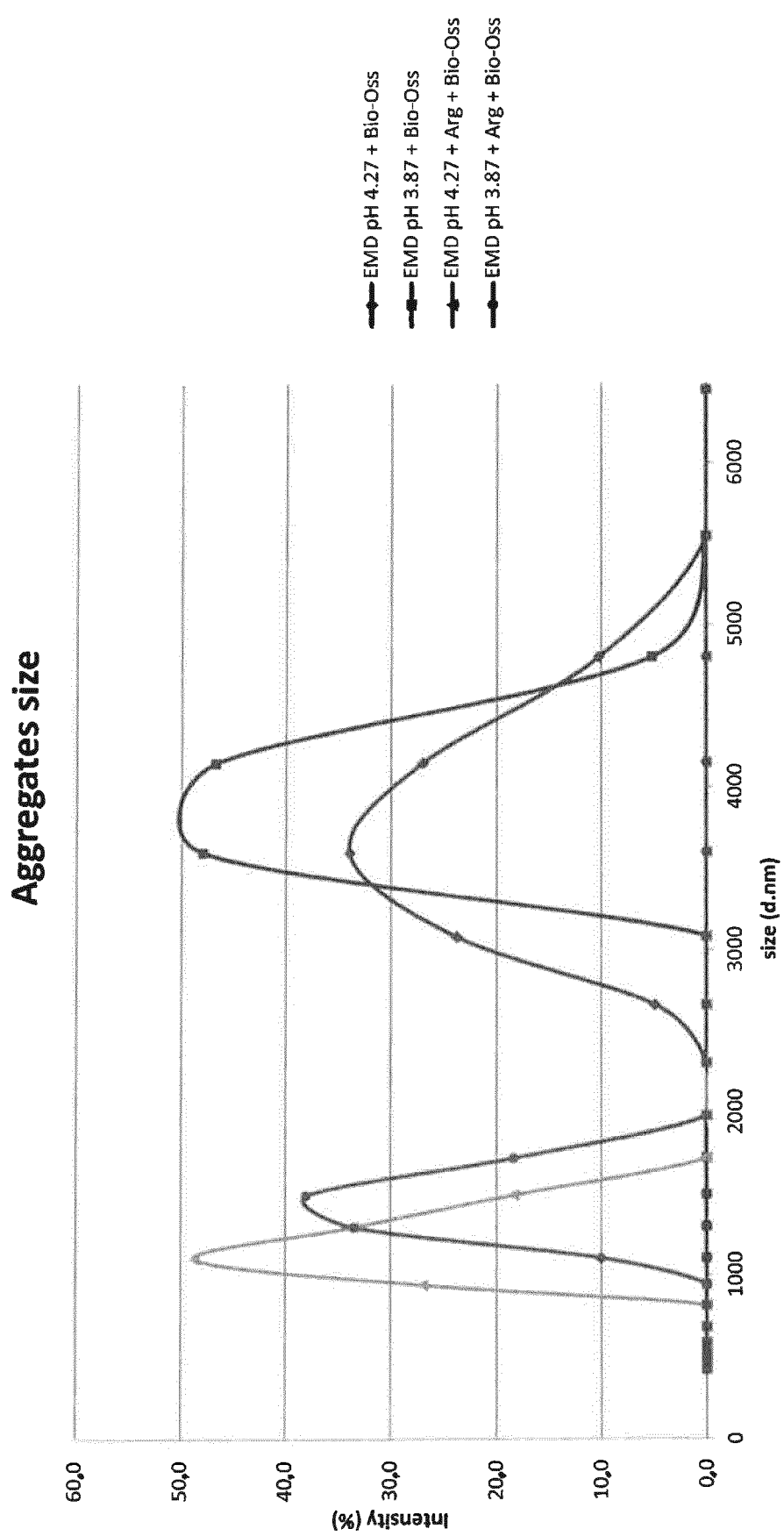

In FIG. 8, the size distribution of EMD solutions with and without arginine, in presence of Bio-Oss®, are shown. More precisely, it seems that when arginine is added to a solution with Bio-Oss® at pH higher than 4, it lowers the size of the precipitates but increases their number. The opposite is also true for EMD solutions with Bio-Oss® at pH lower than 4.

2.1.4 Scanning Electron Microscopy (SEM)

Figure 9:
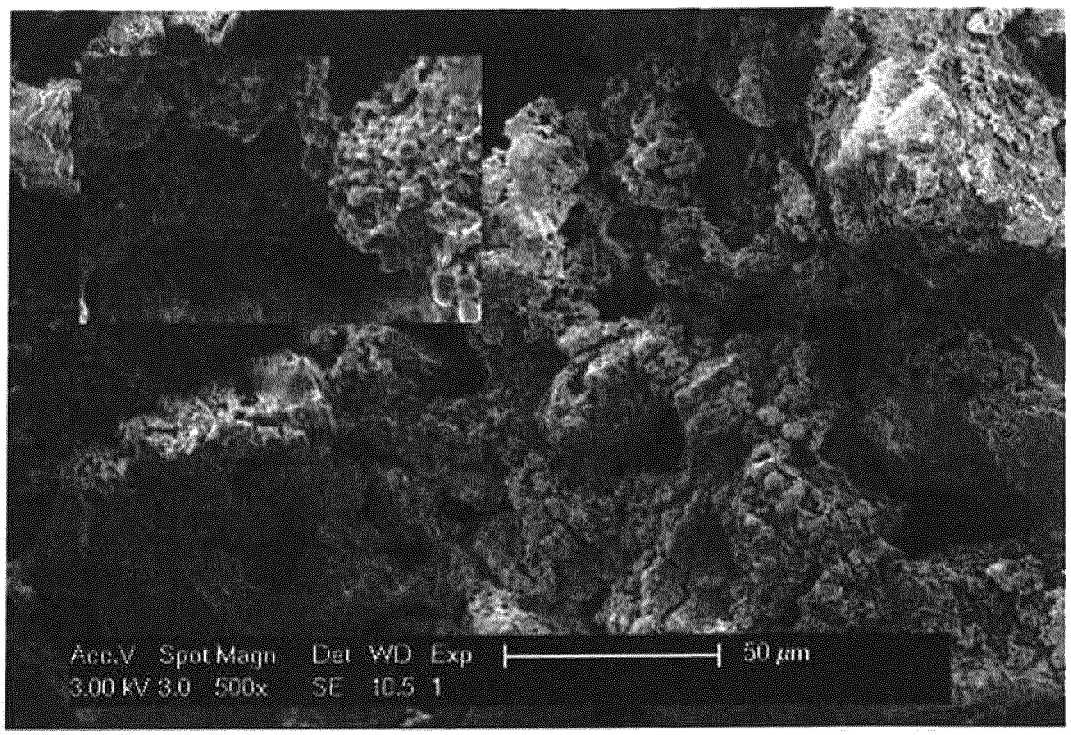

In FIG. 9 is presented an image of EMD solution at initial pH 4.27 with Bio-Oss® granules obtained by scanning electron microscopy. It is possible to observe EMD aggregates with a globular shape that covers most of the surface of the granules after precipitation.

2.2 Oss Solutions 2.2.1 pH Evolution

Figure 10:
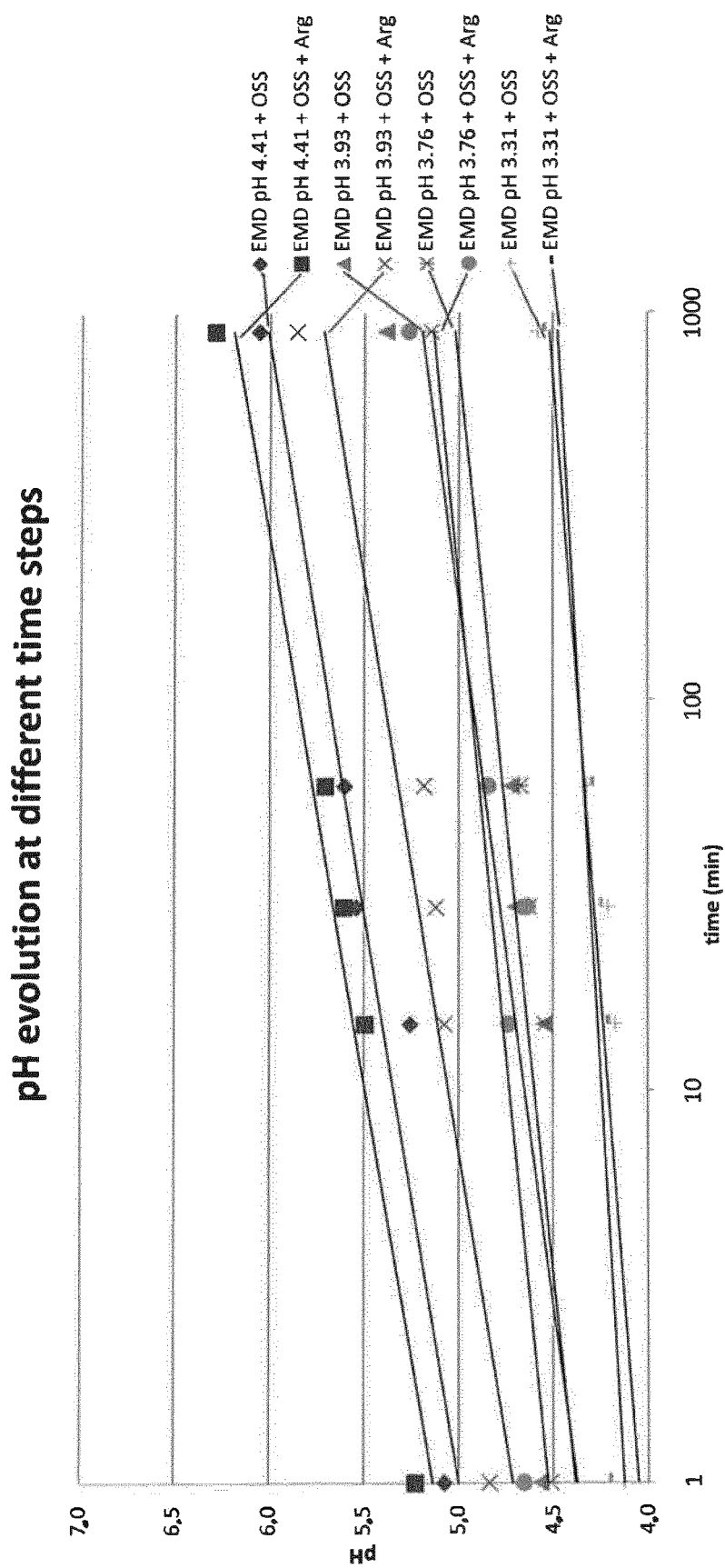

FIG. 10 shows the pH variation of solutions of EMD mixed with Oss at pH 4.41, 3.93, 3.76, and 3.31 with and without arginine. It is noticeable that between two and three hours, the samples at pH 4.41 are the first to reach a pH value of 6, which causes EMD precipitation due to the vicinity to the isoelectric point of amelogenin (pH 6.8). Even if it is not shown on the graph, the solutions at pH 3.93, 3.76, and 3.31, reached the pH value of 6 respectively after 15 hours, 5 days, and 8 days. When arginine is added to the solutions, it increases the velocity at which the pH evolves. As in the case of Bio-Oss®, the precipitation of the EMD particles has to occur within reasonable times, this is why only the solution at pH 4.41 will be considered in the following results regarding Oss granules.

2.2.2 Fluorescence

Figure 11:
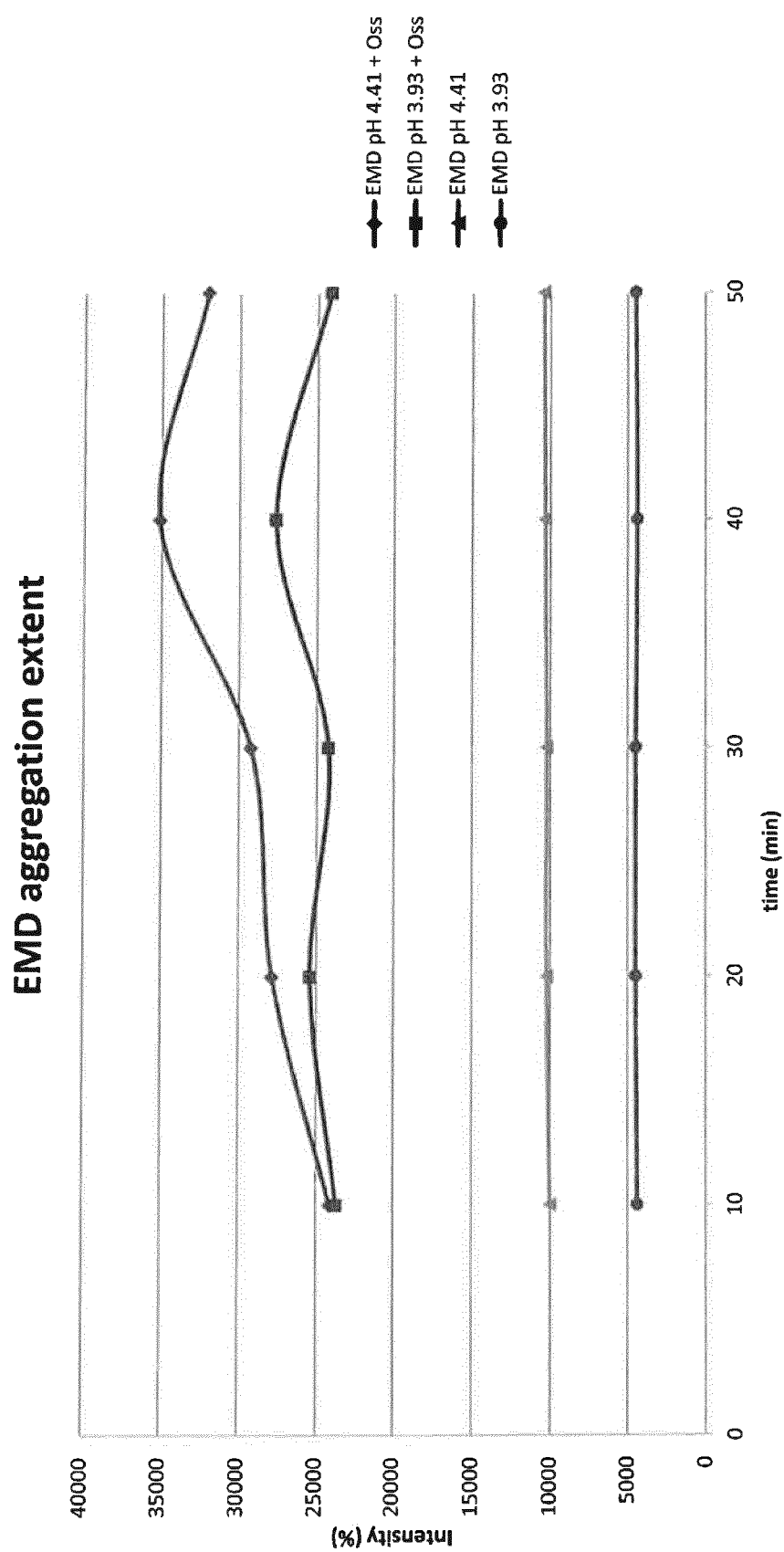

FIG. 11 shows the fluorescence intensity of EMD in acetic acid with and without Oss granules at different pH. When increasing the pH of the solutions, the signal intensity raises, meaning that more aggregates are present. On the other hand, the solutions containing the scaffold exhibit a higher intensity than the samples without it, because aggregation is fast since the pH increase is again favored up to precipitation. Finally, the EMD in acetic acid solutions have a constant signal in time, hence no aggregation occurs, while the ones containing Oss are undergoing a lot of oscillations.

Figure 12:
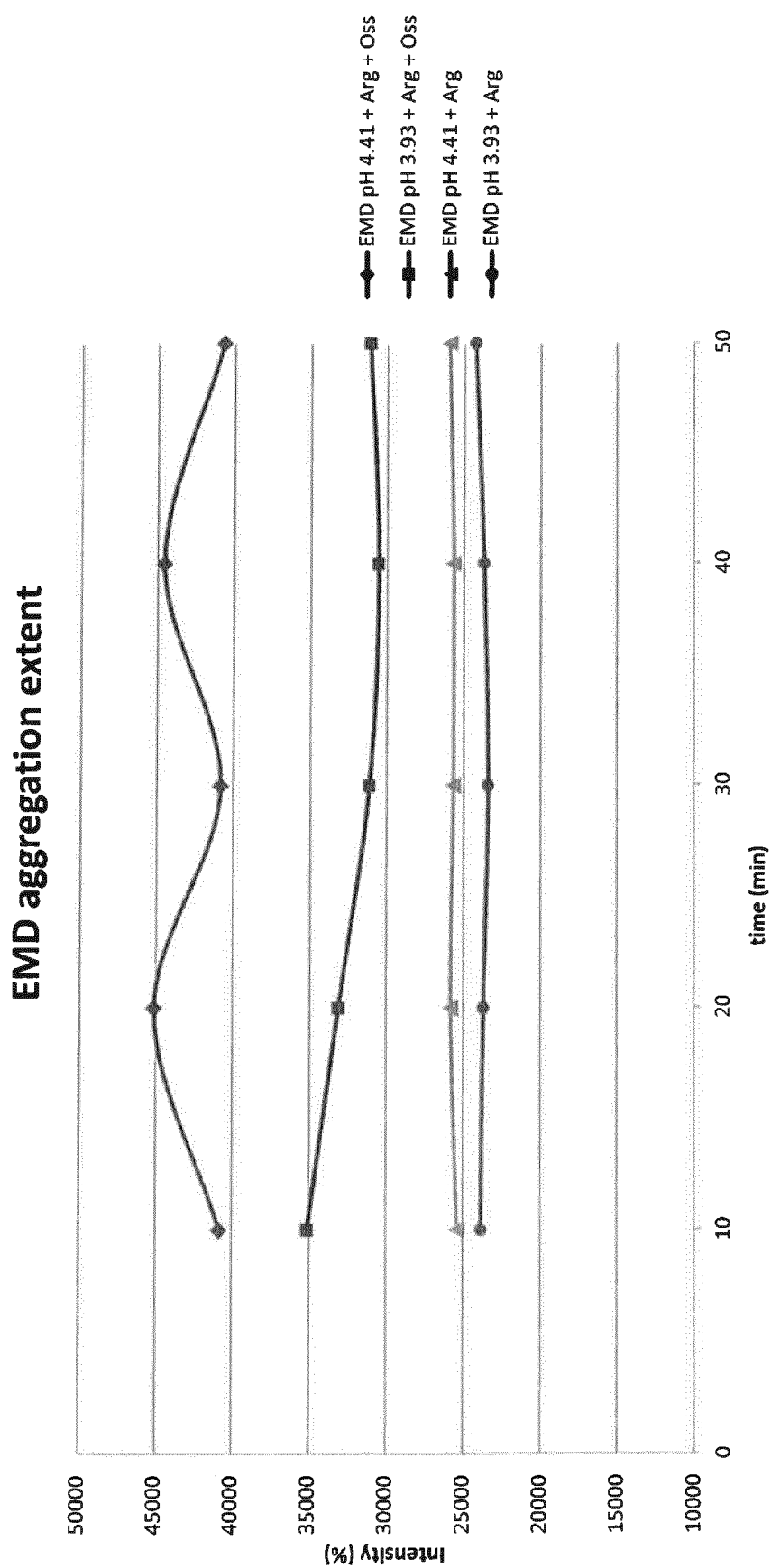

FIG. 12 shows the fluorescence intensity of EMD in acetic acid and arginine with and without Oss at different pH. It is noticeable that the solutions containing Oss have a higher intensity signal than the ones without. As in FIG. 11, the solutions without Oss have a signal intensity that stays almost constant in time, whereas the solutions with Oss show an oscillating signal. As a general trend for the solutions without Oss, when the pH of the solution increased, the fluorescence signal is higher. Finally, when comparing with FIG. 11, it is noticeable that the addition of arginine does that the signal intensity values for EMD solutions with Oss are increasing a lot.

2.2.3 Dynamic Light Scattering (DLS)

Figure 13:
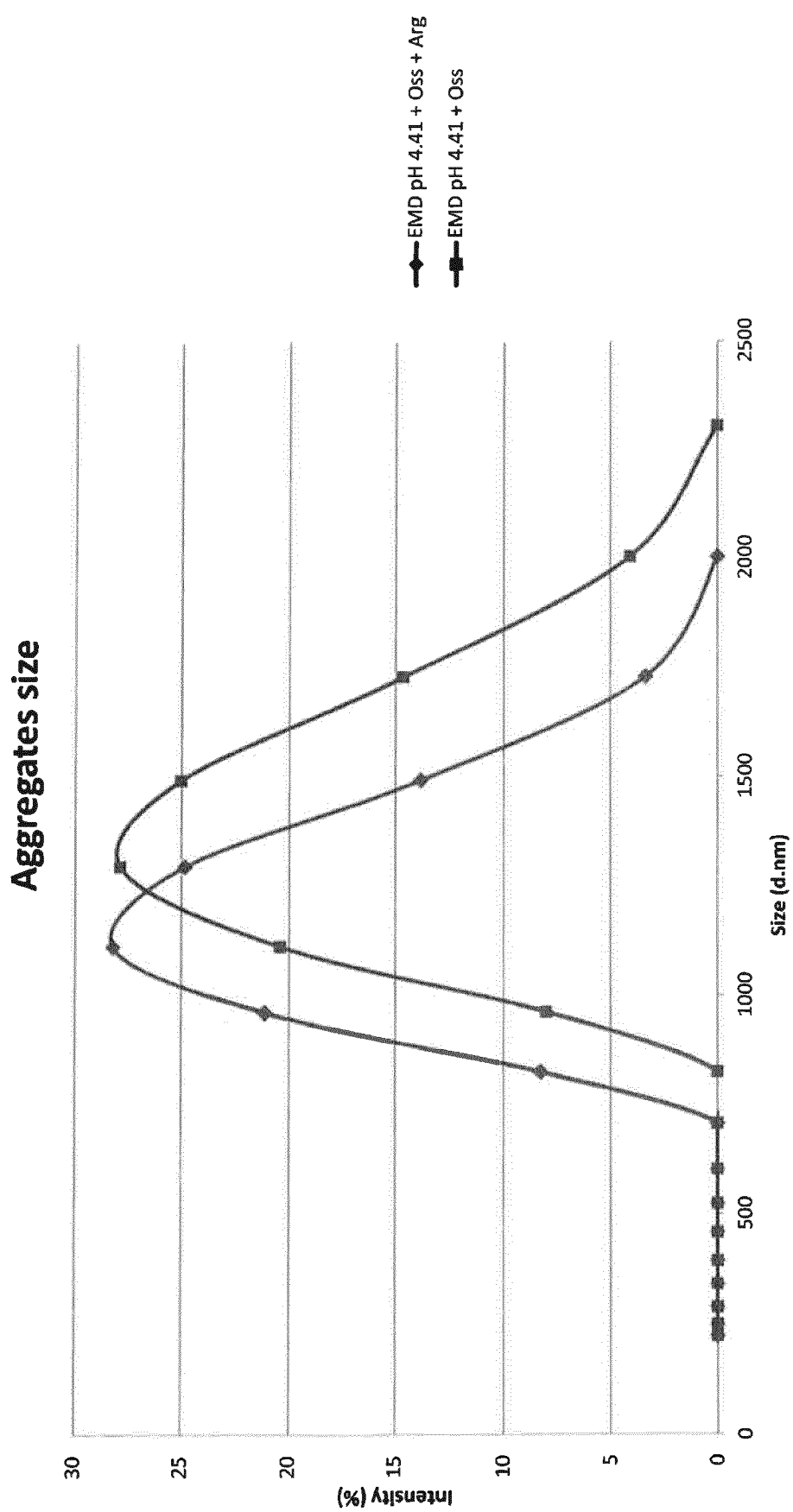

In FIG. 13, DLS curves of EMD diluted in acetic acid samples with Oss at pH 4.41 are represented. It is noticeable that the addition of arginine to the solution shifts the size distribution to lower values but its intensity remains unchanged.

2.2.4 Scanning Electron Microscopy (SEM)

Figure 14:
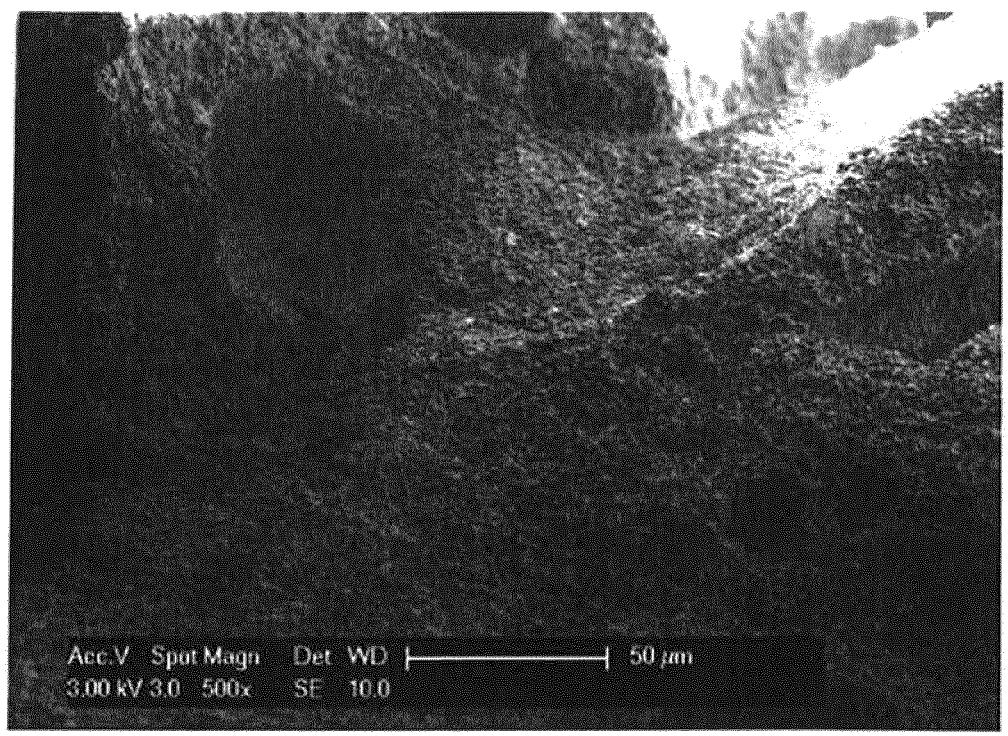

FIG. 14 shows a scanning electron microscopy image of an EMD solution at initial pH 4.41 containing Oss granules. After precipitation, it is possible to observe that there are no EMD particles aggregates that are present on the surface of the granules.

3. Discussion

By analyzing the pH evolution of the EMD solutions with and without arginine and Bio-Oss® or Oss granules presented in (FIGS. 2 & 10), it is visible that the Bio-Oss® granules favor the precipitation of EMD particles more than Oss. This application would require a certain time needed by the dentist to apply the product before the precipitation of EMD particles occurs. The solution at pH 4.27 in presence of Bio-Oss® precipitates too fast (<10 minutes), but the solution at pH 3.87 is a bit too slow (over 100 minutes), indeed the equilibrium should be found between these two initial pH. On the other hand, the solution at pH 4.41 in presence of Oss precipitates in more than 100 minutes, which is as previously mentioned too slow for this application.

The fluorescence intensity measurements that were performed have shown the evolution of EMD aggregation in time. Independently of the pH, EMD solutions with and without arginine always show a fluorescence intensity signal that remains constant on the overall time scale, meaning that no aggregation occurs (FIGS. 3, 4, 11, & 12). When Bio-Oss® granules are added to the solution in absence of arginine, the signal increases in time indicating EMD aggregation. This behavior is not observed when arginine is present, because the signal is only slightly increasing or constant, depending on the analyzed solution. On the other hand, when Oss granules are added to the solution with or without arginine, the signal is almost always oscillating, which indicates aggregation and disaggregation stages. These observations permit to deduce that arginine tends to reduce the amount of EMD aggregates that are formed in presence of Bio-Oss®, while it increases their number when Oss granules are present. The results also indicate that Bio-Oss® permits a more stable and continuous aggregation of EMD than Oss. This might be related to the fact that due to the lower porosity of Oss, the EMD particles do not manage to adsorb and be integrated by the scaffold granules (FIG. 14).

When focusing on the dynamic light scattering analysis performed to obtain the distributions of EMD aggregates in solution with different additives, there are several pieces of information that can be deduced. In FIG. 5 it is visible that the size of EMD aggregates is nearly 100 nm, which corresponds to amelogenin nanospheres. Besides, the distribution is slightly large because previous investigations have shown that EMD form oligomers in solution. On the same graph, a shoulder appears when arginine is added to EMD solutions, and this might indicate that also arginine forms aggregates having 30 to 50 nm diameter size. Differently, when the two scaffolds are added to EMD solutions, the addition of arginine always lowers the size of the aggregates, meaning that it probably limits the unfolding of the proteins, which will result in a more compact structure (FIGS. 8 & 13). This last point is crucial, because as briefly explained in the beginning of the report, unfolded aggregates are useless for the tissue regeneration. Finally, it is noticeable that for a given pH, EMD aggregates are bigger in presence of Bio-Oss® than Oss granules, probably because the precipitation is reached faster in the first case (FIGS. 2 and 10).

4. Conclusion

Throughout this project, several experiments have been conducted on Enamel Matrix Derivative (EMD) solutions combined to two different scaffolds, Bio-Oss® and Oss. The effect of the initial pH of the solutions and the effect of arginine, an amino acid already used in dentistry, have been investigated for understanding their role on the aggregation and precipitation kinetics of the EMD particles. In addition to the pH measurements, dynamic light scattering and fluorescence intensity experiments have been performed respectively to measure the size of the precipitates and their amount. Lastly, scanning electron microscopy imaging was carried out on the granules with the interest to evaluate their surface coverage by EMD precipitates and their morphology. These different investigations permit to deduce the best conditions for the regenerative scaffold for periodontal tissues, which are an EMD solution initial pH included between 3 and 4, and a scaffold composed of Bio-Oss® granules. It has also been proven that arginine limits EMD unfolding during long time storage, and this is crucial in pursuance of guaranteeing the healing ability of the product, avoiding any degradation mechanisms that might compromise its stability and efficiency.

Experiment 2

Viscosity Measurement of Osteogain®

The goal of this experiment was to measure the viscosity of a composition comprising active enamel proteins (Osteogain®) in acetic acid.

An Ostwald viscometer from Sigma Aldrich (art no. Z 275409-1 EA) was used. Other material used was milliQ water, Osteogain® solution (30 mg EMD/ml).

2.1 Performance of Measurement 10 ml solution (water or Osteogain®) was transferred to the viscometer. The time for the solution to pass through the viscometer was determined with the stop watch. Two measurements were performed per solution (water and Osteogain®). The expected outflow time for water at 20° C. is 80-100 s.

2.2 Results

TABLE 1

| Solution | Measurement 1 (s) | Measurement 2 (s) | Average (s) |
|---|---|---|---|
| Water | 102 | 103 | 102.5 |
| Osteogain | 184 | 188 | 186 |

The time for Osteogain® is 1.8 times longer than the time for water. Since the difference in density for Osteogain® and water is neglectable, the viscosity for Osteogain is 1.8 times higher than for water. The viscosity for water at 22° C. is 0.9548 cP (according to Handbook of Chemistry and Physics $64^{th}$ edition table F-38) giving the viscosity for Osteogain as 1.7 cP (i.e. 1.7 m Pa·s at 22° C. (RT)).

2.3 Conclusion

The viscosity of Osteogain® is 1.8 times the viscosity of water.

The water viscosity at 22° C. is 0.9548 cP giving the viscosity of Osteogain as 1.7 cP.

In comparison to EMDOGAIN®, which has a viscosity of 3000 cP (3000 m Pa·s at 22° C. (RT)), the Osteogain® solution is several magnitudes less viscous.

LIST OF REFERENCES 1. http://www.straumann.us/en/professionals/products-and-solutions/regenerationsolution/tissue-regeneration.html, How Emdogain regenerates the periodontium, c 2014 Institut Straumann AG
2. Dannan, A. et al., In vitro studies of Enamel Matrix Derivative In Terms of Periodontal Wound Healing and Periodontal Regeneration, The Internet Journal of Dental Science, 2008
3. Wanner, H., Biofunctionality of Geistlich Bio-Oss® Outstanding hydrophilicity—a key factor for clinical success
4. Apicella, A. et al., Injectable scaffolds for periodontal tissues regeneration, Ecole Polytechnique Federate de Lausanne (EPFL), 2014
5. Dumitrescu, A. L., Chemicals in Surgical Periodontal Therapy—Bone Grafts and Bone Graft Substitutes in Periodontal Therapy, Springer, 2011
6. Schmid, F., Biological Macromolecules: UV-visible spectrophotometry, University of Bayreuth, Germany, 2001
7. Apicella, A. et al., Arginine promotes stability in enamel matrix derivative (EMD) proteins: a way to prolong the shelf life of EMD-based products, Submitted 2014
8. Arzensek, D., Dynamic light scattering and application to proteins in solutions, Department of Physics, University of Ljubljana, May 2010
9. Schein, C., Protein aggregation and precipitation, measurement and control, University of Texas Medical Branch, Texas, 2010
10. Handbook of Chemistry and Physics $64^{th}$ edition.

The invention claimed is:

1. A composition for bioactivating a bone graft material, said composition comprising isolated enamel matrix derivative proteins at a concentration of 0.3 mg/ml-100 mg/ml in a suitable pharmaceutical carrier selected from the group consisting of citric acid, acetic acid, tartaric acid, lactic acid and hydrogenphosphoric acid, said composition having a pH between pH 3.8-4.2, and a viscosity of less than 50 mPa s at 22° C.

2. The composition according to claim 1, said composition having a pH between pH 3.8-4.2, and a viscosity between 30-1 mPa s at 22° C.

3. The composition according to claim 1, said composition having a pH between pH 3.8-4.2, and a viscosity between 2.5-1.2 mPa s at 22° C.

4. The composition according to claim 1, said composition having a pH of 4.0, and a viscosity of 1.7 mPa s at 22° C.

5. The composition according to claim 1, wherein the concentration of enamel matrix proteins is 29-31 mg/ml.

* * * * *